US011219719B2

(12) United States Patent
Brady et al.

(10) Patent No.: US 11,219,719 B2
(45) Date of Patent: Jan. 11, 2022

(54) VOLUME MONITORING SYSTEMS

(71) Applicant: Osprey Medical, Inc., Minnetonka, MN (US)

(72) Inventors: Dale Brady, New Brighton, MN (US); Rodney L. Houfburg, Prior Lake, MN (US); Steve Rathjen, South Lake Tahoe, CA (US)

(73) Assignee: Osprey Medical, Inc., Minnetonka, MN (US)

( * ) Notice: Subject to any disclaimer, the term of this patent is extended or adjusted under 35 U.S.C. 154(b) by 0 days.

(21) Appl. No.: 15/089,061

(22) Filed: Apr. 1, 2016

(65) Prior Publication Data
US 2016/0213834 A1 Jul. 28, 2016

Related U.S. Application Data

(63) Continuation-in-part of application No. 14/222,331, filed on Mar. 21, 2014, now Pat. No. 9,999,718,
(Continued)

(51) Int. Cl.
*A61M 5/315* (2006.01)
*A61M 5/145* (2006.01)
*A61M 5/168* (2006.01)

(52) U.S. Cl.
CPC .... *A61M 5/31573* (2013.01); *A61M 5/31568* (2013.01); *A61M 5/1452* (2013.01);
(Continued)

(58) Field of Classification Search
CPC .......... A61M 5/31568; A61M 5/31573; A61M 2205/3317; A61M 2205/3379;
(Continued)

(56) References Cited

U.S. PATENT DOCUMENTS 550,747 A 12/1895 De Zeng, Jr.
3,469,578 A 9/1969 Bierman
(Continued)

FOREIGN PATENT DOCUMENTS

DE 19643813 A1 4/1998
EP 0523343 1/1993
(Continued)

OTHER PUBLICATIONS

Davies, Justin E. et al., "Evidence of a Dominant Backward-Propagating 'Suction' Wave Responsible for Diastolic Coronary Filling in Humans, Attenuated in Left Ventricular Hypertrophy" (Circulation. 2006;113:1768-1778).
(Continued)

*Primary Examiner* — Nilay J Shah
(74) *Attorney, Agent, or Firm* — Merchant & Gould P.C.

(57) ABSTRACT

An apparatus has a syringe housing and a plunger having a shaft, wherein the plunger is slidably received within the syringe housing between a first and second position. A plurality of Hall sensors are disposed on the shaft. A circuit board is also disposed on the shaft. A battery is disposed on the shaft. A wireless transmitter is disposed on the shaft and provides wireless communication between a Hall sensor and a signal processing device. At least one magnet is fixed proximate the syringe housing.

27 Claims, 27 Drawing Sheets

Related U.S. Application Data which is a continuation-in-part of application No. 13/975,052, filed on Aug. 23, 2013, now Pat. No. 10,413,677, which is a continuation-in-part of application No. 13/839,771, filed on Mar. 15, 2013, now Pat. No. 9,320,846, application No. 15/089,061, which is a continuation-in-part of application No. 14/851,958, filed on Sep. 11, 2015, now Pat. No. 10,022,497, which is a continuation-in-part of application No. 13/839,771, filed on Mar. 15, 2013, now Pat. No. 9,320,846.

(60) Provisional application No. 62/141,723, filed on Apr. 1, 2015, provisional application No. 61/694,137, filed on Aug. 28, 2012, provisional application No. 62/082,260, filed on Nov. 20, 2014, provisional application No. 62/048,974, filed on Sep. 11, 2014.

(52) U.S. Cl.
CPC ... *A61M 5/1684* (2013.01); *A61M 2205/3306* (2013.01); *A61M 2205/3317* (2013.01); *A61M 2205/3379* (2013.01); *A61M 2205/3389* (2013.01); *A61M 2205/702* (2013.01)

(58) Field of Classification Search
CPC .......... A61M 2205/3389; A61M 5/315; A61M 5/31525; A61M 5/31565; A61M 5/31571; A61M 5/3157; A61M 2207/00; A61M 2207/10

See application file for complete search history.

(56) References Cited

U.S. PATENT DOCUMENTS

| | | | |
|---|---|---|---|
| 3,543,759 A | 12/1970 | McWhorter | |
| 3,556,122 A | 1/1971 | Laerdal | |
| 3,572,375 A | 3/1971 | Rosenberg | |
| 3,626,978 A | 12/1971 | Hoekstra | |
| 3,633,613 A | 1/1972 | Julow | |
| 3,661,174 A | 5/1972 | Cripe | |
| 3,695,575 A | 10/1972 | Hauser | |
| 3,818,929 A | 6/1974 | Braukmann | |
| 3,905,382 A | 9/1975 | Waterston | |
| 3,941,149 A | 3/1976 | Mittleman | |
| 3,958,573 A * | 5/1976 | Wiley .................. | A61C 17/04 604/267 |
| 3,985,141 A | 10/1976 | Stanley et al. | |
| 4,000,741 A | 1/1977 | Binard et al. | |
| 4,006,736 A | 2/1977 | Kranys et al. | |
| 4,030,497 A | 6/1977 | Binard et al. | |
| 4,044,793 A | 8/1977 | Krueger et al. | |
| 4,074,714 A | 2/1978 | Binard et al. | |
| 4,077,405 A | 3/1978 | Haerten et al. | |
| 4,084,606 A | 4/1978 | Mittleman | |
| 4,136,708 A | 1/1979 | Cosentino et al. | |
| 4,142,525 A | 3/1979 | Binard et al. | |
| 4,147,170 A | 4/1979 | Taylor | |
| 4,240,430 A | 12/1980 | Binard et al. | |
| 4,289,006 A | 9/1981 | Hallengren | |
| 4,318,400 A | 3/1982 | Peery et al. | |
| 4,329,985 A | 5/1982 | Bonchek | |
| 4,381,006 A | 4/1983 | Genese | |
| 4,392,847 A | 7/1983 | Whitney et al. | |
| 4,403,988 A | 9/1983 | Binard et al. | |
| 4,457,751 A | 7/1984 | Rodler | |
| 4,481,008 A | 11/1984 | Kurtz | |
| 4,501,291 A | 2/1985 | Siegrist | |
| 4,502,502 A | 3/1985 | Krug | |
| 4,602,700 A | 7/1986 | Szabo | |
| 4,655,746 A | 4/1987 | Daniels et al. | |
| 4,671,786 A | 6/1987 | Krug | |
| 4,744,786 A | 5/1988 | Hooven | |
| 4,755,172 A | 7/1988 | Baldwin | |
| 4,758,223 A | 7/1988 | Rydell | |
| 4,795,431 A | 1/1989 | Walling | |
| 4,813,937 A | 3/1989 | Vaillancourt | |
| 4,838,857 A | 6/1989 | Strowe et al. | |
| 4,845,493 A * | 7/1989 | Howard ............... | E21B 47/011 324/323 |
| 4,867,743 A | 9/1989 | Vaillancourt | |
| 4,997,420 A | 3/1991 | LeFevre | |
| 5,059,174 A | 10/1991 | Vaillancourt | |
| 5,094,148 A | 3/1992 | Haber et al. | |
| 5,139,484 A | 8/1992 | Hazon et al. | |
| 5,167,631 A | 12/1992 | Thompson et al. | |
| 5,273,187 A | 11/1993 | Suzuki | |
| 5,376,785 A | 12/1994 | Chin et al. | |
| 5,460,609 A | 10/1995 | O'Donnell | |
| 5,534,691 A | 7/1996 | Holdaway et al. | |
| 5,556,386 A | 9/1996 | Todd | |
| 5,573,515 A | 11/1996 | Wilson et al. | |
| 5,575,767 A | 11/1996 | Stevens | |
| 5,662,612 A | 9/1997 | Niehoff | |
| 5,681,285 A | 10/1997 | Ford | |
| 5,685,851 A | 11/1997 | Murphy et al. | |
| 5,707,356 A | 1/1998 | Paul | |
| 5,752,940 A | 5/1998 | Grimard | |
| 5,785,681 A | 7/1998 | Indravudh | |
| 5,792,117 A | 8/1998 | Brown | |
| 5,799,700 A | 9/1998 | Teh et al. | |
| 5,800,397 A | 9/1998 | Wilson et al. | |
| 5,806,519 A | 9/1998 | Evans, III et al. | |
| 5,807,321 A | 9/1998 | Stoker | |
| 5,827,941 A | 10/1998 | Good et al. | |
| 5,840,026 A | 11/1998 | Uber, III et al. | |
| 5,840,071 A | 11/1998 | Kriesel et al. | |
| 5,882,338 A | 3/1999 | Gray | |
| 5,882,343 A | 3/1999 | Wilson et al. | |
| 5,885,216 A | 3/1999 | Evans, III et al. | |
| 5,916,165 A | 6/1999 | Duchon et al. | |
| 5,954,700 A * | 9/1999 | Kovelman ......... | A61M 5/31525 604/189 |
| 6,019,747 A | 2/2000 | McPhee | |
| 6,086,559 A | 7/2000 | Enk | |
| 6,113,578 A | 9/2000 | Brown | |
| 6,159,180 A | 12/2000 | Kriesel et al. | |
| 6,270,481 B1 | 8/2001 | Mason | |
| 6,317,623 B1 | 11/2001 | Griffiths et al. | |
| 6,397,098 B1 | 5/2002 | Uber, III et al. | |
| 6,409,699 B1 | 6/2002 | Ash | |
| 6,442,418 B1 | 8/2002 | Evans, III et al. | |
| 6,558,125 B1 | 5/2003 | Futterknecht | |
| 6,645,177 B1 | 11/2003 | Shearn | |
| 6,850,792 B2 | 2/2005 | Ohishi | |
| 6,858,020 B2 | 2/2005 | Rusnak | |
| 6,866,654 B2 | 3/2005 | Callan et al. | |
| 6,889,074 B2 | 5/2005 | Uber, III et al. | |
| 6,901,283 B2 | 5/2005 | Evans, III et al. | |
| 6,966,893 B2 | 11/2005 | Holtby et al. | |
| 6,969,353 B2 | 11/2005 | Brock-Fisher et al. | |
| 6,970,735 B2 | 11/2005 | Uber, III et al. | |
| 7,022,107 B1 | 4/2006 | Christensen et al. | |
| 7,065,395 B2 | 6/2006 | Lienard et al. | |
| 7,094,216 B2 | 8/2006 | Trombley, III et al. | |
| 7,255,684 B2 | 8/2007 | Zubry | |
| 7,270,648 B2 | 9/2007 | Kazemzadeh | |
| 7,326,186 B2 | 2/2008 | Trombley, III et al. | |
| 7,470,253 B2 | 12/2008 | Kriesel et al. | |
| 7,516,760 B2 | 4/2009 | Weber | |
| 7,559,483 B2 | 7/2009 | Hickle | |
| 7,611,503 B2 | 11/2009 | Spohn et al. | |
| 7,618,412 B2 | 11/2009 | Chernack | |
| 7,678,070 B2 | 3/2010 | Kumar et al. | |
| 7,766,885 B2 | 8/2010 | Olsen | |
| 7,815,604 B2 | 10/2010 | Massengale et al. | |
| 7,854,726 B2 | 12/2010 | Fago et al. | |
| 7,925,330 B2 | 4/2011 | Kalafut et al. | |
| 7,927,305 B2 | 4/2011 | Yribarren et al. | |
| 7,951,129 B2 | 5/2011 | Chinchoy | |
| 7,955,301 B1 | 6/2011 | McKay | |
| 8,075,490 B2 | 12/2011 | Lofgren et al. | |

(56) References Cited

U.S. PATENT DOCUMENTS

| | | |
|---|---|---|
| 8,147,448 B2 | 4/2012 | Sundar et al. |
| 8,172,790 B2 | 5/2012 | Hunter et al. |
| 8,197,443 B2 | 6/2012 | Sundar et al. |
| 8,197,444 B1 | 6/2012 | Bazargan et al. |
| 8,208,994 B2 | 6/2012 | Niethammer |
| 8,257,310 B2 | 9/2012 | Donovan et al. |
| 8,295,914 B2 | 10/2012 | Kalafut et al. |
| 8,303,547 B2 | 11/2012 | Brown |
| 8,323,267 B2 | 12/2012 | Haase |
| 8,328,758 B2 | 12/2012 | Childers et al. |
| 9,320,846 B2 | 4/2016 | Burns et al. |
| 2001/0039396 A1 | 11/2001 | Kriesel et al. |
| 2002/0087125 A1 | 7/2002 | Pokorney |
| 2002/0128611 A1 | 9/2002 | Kandalaft |
| 2002/0198496 A1 | 12/2002 | Duchon |
| 2003/0055380 A1 | 3/2003 | Flaherty |
| 2003/0233069 A1 | 12/2003 | Gillespie, Jr. et al. |
| 2004/0015123 A1 | 1/2004 | Smith |
| 2004/0135078 A1 | 7/2004 | Mandro et al. |
| 2004/0138615 A1 | 7/2004 | Lombardi |
| 2004/0143212 A1 | 7/2004 | Trombley et al. |
| 2004/0178255 A1 | 9/2004 | Eich et al. |
| 2004/0226183 A1 | 11/2004 | Sielemann |
| 2005/0020983 A1* | 1/2005 | Schreijag ............... A61D 1/025 604/187 |
| 2005/0059931 A1 | 3/2005 | Garrison et al. |
| 2005/0165364 A1 | 7/2005 | DiMatteo et al. |
| 2005/0277912 A1 | 12/2005 | John |
| 2006/0178632 A1 | 8/2006 | Trombley, III et al. |
| 2007/0060820 A1* | 3/2007 | Lofgren ............... A61B 5/0215 600/481 |
| 2007/0062250 A1 | 3/2007 | Krulevitch et al. |
| 2007/0066939 A1 | 3/2007 | Krulevitch et al. |
| 2007/0093752 A1 | 4/2007 | Zhao et al. |
| 2007/0161970 A1 | 7/2007 | Spohn et al. |
| 2008/0004507 A1 | 1/2008 | Williams, Jr. et al. |
| 2008/0147007 A1 | 6/2008 | Freyman et al. |
| 2008/0154187 A1 | 6/2008 | Krulevitch et al. |
| 2008/0164970 A1 | 7/2008 | Malzahn |
| 2008/0287865 A1 | 11/2008 | Nielsen et al. |
| 2008/0312536 A1 | 12/2008 | Dala-Krishna |
| 2009/0234231 A1 | 9/2009 | Knight et al. |
| 2010/0004571 A1 | 1/2010 | Nilsson et al. |
| 2010/0016796 A1 | 1/2010 | Derichs |
| 2010/0114064 A1 | 5/2010 | Kalafut et al. |
| 2010/0152675 A1 | 6/2010 | McClintock |
| 2010/0211003 A1 | 8/2010 | Sundar et al. |
| 2010/0274180 A1 | 10/2010 | Donovan et al. |
| 2011/0092828 A1 | 4/2011 | Spohn et al. |
| 2012/0024987 A1 | 2/2012 | Nacken |
| 2012/0036937 A1 | 2/2012 | Sprenger et al. |
| 2012/0041427 A1 | 2/2012 | Caffey et al. |
| 2012/0116217 A1 | 5/2012 | Lee-Sepsick et al. |
| 2012/0277661 A1 | 11/2012 | Bernard et al. |
| 2012/0277667 A1 | 11/2012 | Yodat et al. |
| 2012/0283186 A1 | 11/2012 | Adams |
| 2012/0302950 A1 | 11/2012 | Landsman et al. |
| 2012/0316460 A1 | 12/2012 | Stout |
| 2013/0261729 A1 | 10/2013 | Gillick et al. |
| 2014/0066860 A1 | 3/2014 | Houfburg et al. |
| 2014/0066891 A1 | 3/2014 | Burns et al. |
| 2014/0163339 A1 | 6/2014 | Goldstein et al. |
| 2014/0288422 A1 | 9/2014 | Brady et al. |
| 2015/0202361 A1 | 7/2015 | Burns et al. |
| 2015/0202386 A1 | 7/2015 | Brady et al. |
| 2018/0272072 A1 | 9/2018 | Radmer |
| 2018/0318495 A1 | 11/2018 | Brady et al. |
| 2019/0030256 A1 | 1/2019 | Brady |

FOREIGN PATENT DOCUMENTS

| | | |
|---|---|---|
| EP | 1930603 A1 | 6/2008 |
| JP | S62-184302 | 8/1987 |
| JP | H06 296690 A | 10/1994 |
| JP | H09-506288 | 6/1997 |
| JP | 2005-523397 A | 8/2005 |
| JP | 2005-533568 A | 11/2005 |
| JP | 2007-175444 A | 7/2007 |
| WO | WO 84/01718 A1 | 5/1984 |
| WO | WO 89/03230 A1 | 4/1989 |
| WO | WO 96/11024 | 4/1996 |
| WO | WO 98/17974 | 4/1998 |
| WO | 02/064196 A1 | 8/2002 |
| WO | WO 02/098493 A1 | 12/2002 |
| WO | WO 2004/009163 A1 | 1/2004 |
| WO | WO 2005/068848 A1 | 7/2005 |
| WO | WO 2009/039203 | 3/2009 |
| WO | WO 2009/065153 A2 | 5/2009 |
| WO | 2012/167720 | 12/2012 |
| WO | 2013/177135 | 11/2013 |
| WO | WO 2014/035647 | 3/2014 |
| WO | 2016/040949 | 3/2016 |

OTHER PUBLICATIONS

PCT International Search Report and Written Opinion in International Application PCT/US2013/054510, dated Dec. 4, 2013, 16 pgs.

PCT International Search Report and Written Opinion in International Application PCT/US2014/052319, dated Feb. 5, 2015, 14 pgs.

PCT International Search Report and Written Opinion in International Application PCT/US2015/021294, dated Jun. 19, 2015, 13 pgs.

PCT International Search Report and Written Opinion in International Application PCT/US2016/025302, dated Jul. 20, 2016, 13 pgs.

International Search Report and Written Opinion of the International Searching Authority for corresponding International Patent Application No. PCT/US2016/025671 dated Jul. 26, 2016, 16 pgs.

Cigarroa, R et al., "Dosing of Contrast Material to Prevent Contrast Nephropathy in Patients with Renal Disease", The American Journal of Medicine, 86: 649-652 (1989).

Gurm, H. et al., "Renal-Function-Based Contrast Dosing to Define Safe Limits of Radiographic Contrast Media in Patients Undergoing Percutaneous Coronary Interventions", Journal of the American College of Cardiology, 58(9): 907-914 (2011).

PCT International Search Report and Written Opinion in International Application PCT/US2018/040514, dated Sep. 12, 2018, 18 pgs.

PCT International Search Report and Written Opinion in International Application PCT/US2020/027670, dated Jun. 30, 2020, 15 pgs.

* cited by examiner

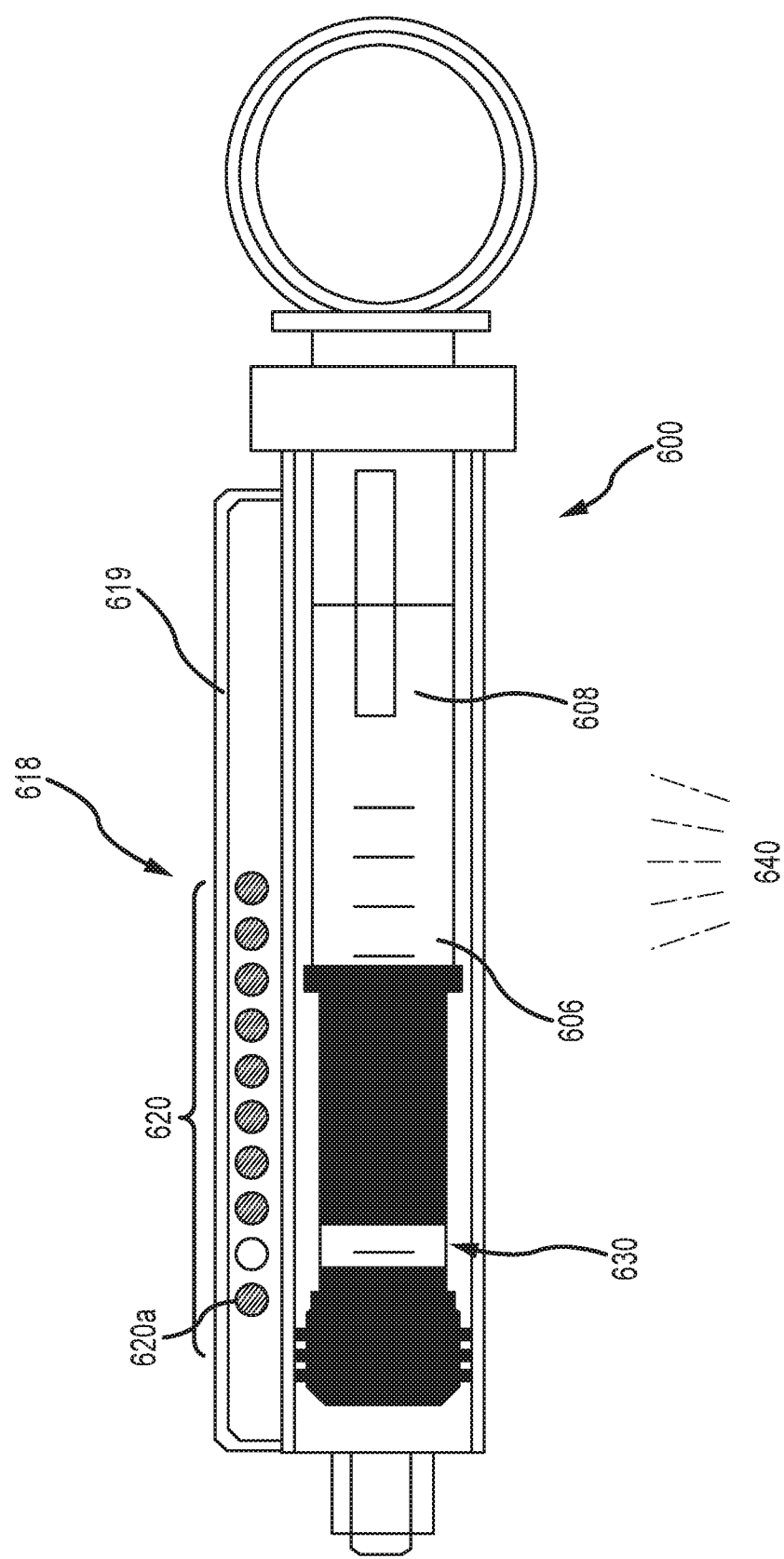

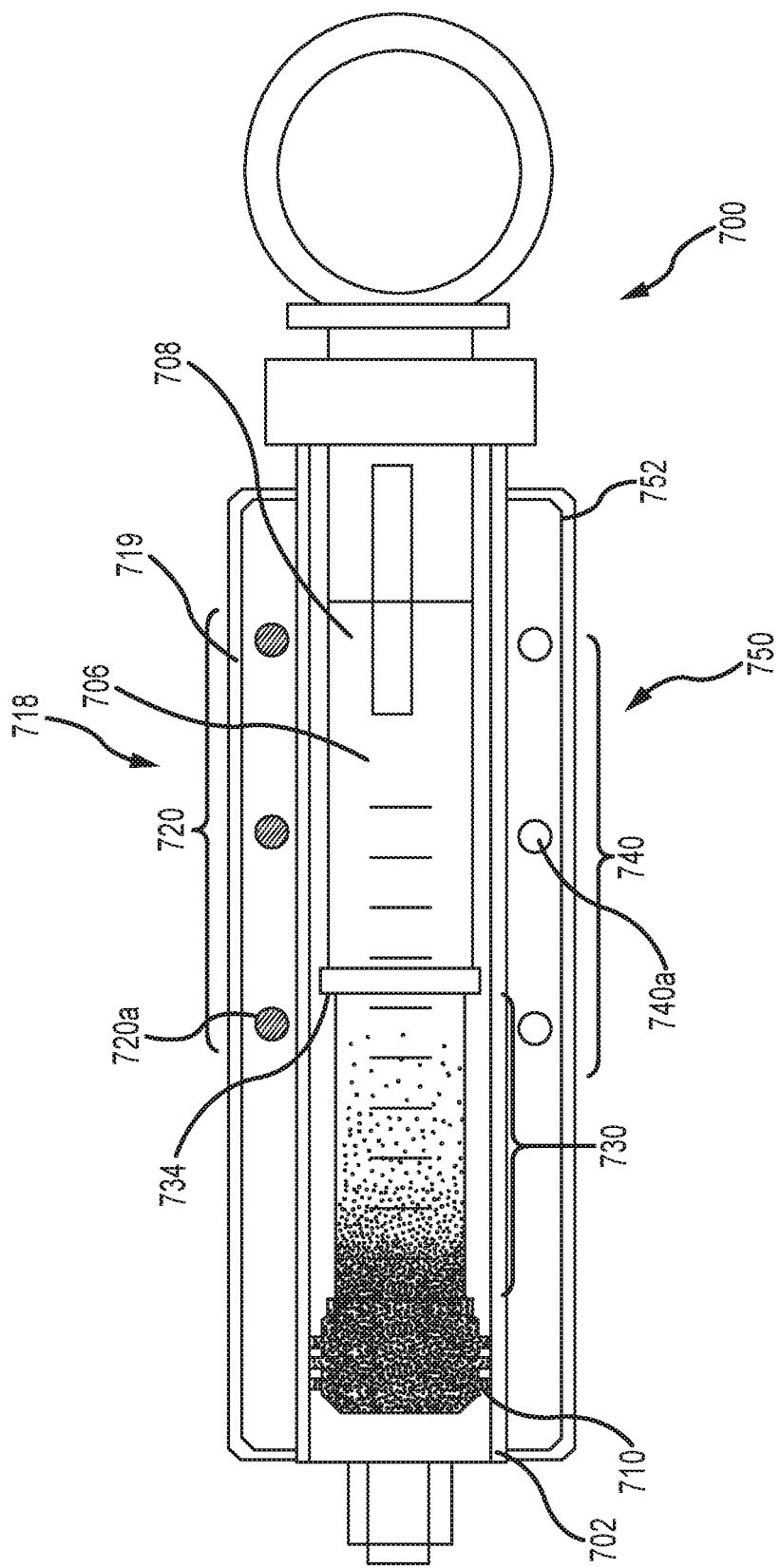

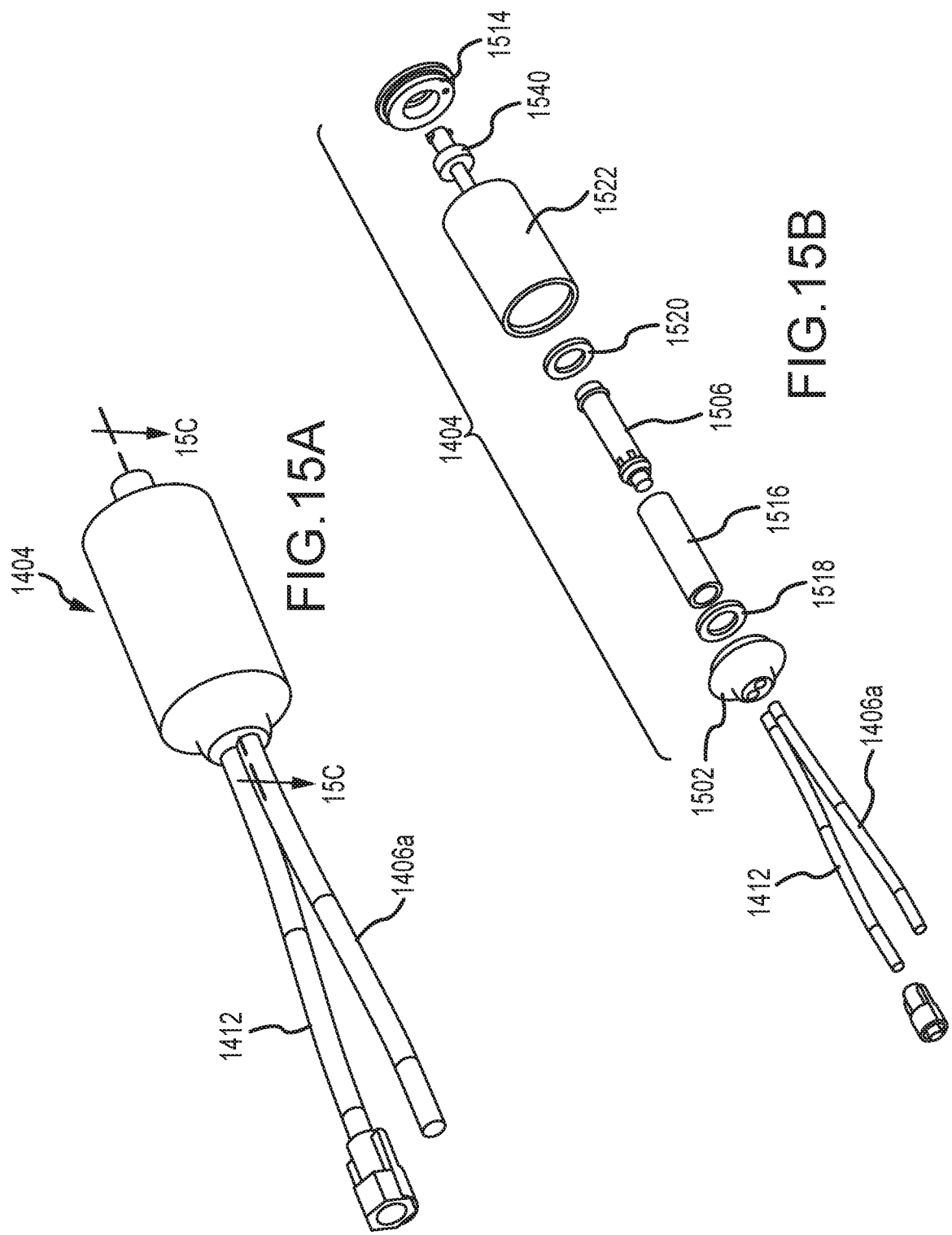

VOLUME MONITORING SYSTEMS

CROSS-REFERENCE TO RELATED APPLICATIONS

This application claims priority to and the benefit of U.S. Patent Application Ser. No. 62/141,723, filed Apr. 1, 2015, entitled "Volume Monitoring Device Utilizing Hall Sensors". This application is also a continuation-in-part of U.S. patent application Ser. No. 14/222,331, filed Mar. 21, 2014, entitled "Volume Monitoring Device Utilizing Light Based Systems"; which is a continuation-in-part of U.S. patent application Ser. No. 13/975,052, filed Aug. 23, 2013, entitled "Volume Monitoring Device"; which is a continuation-in-part of U.S. patent application Ser. No. 13/839,771, filed Mar. 15, 2013, entitled "Devices and Methods for Modulating Medium Delivery"; which claims priority to and the benefit of U.S. Provisional Application Ser. No. 61/694,137, filed Aug. 28, 2012, entitled "Devices and Methods for Modulating Medium Delivery." This application is also a continuation-in-part of U.S. patent application Ser. No. 14/851,958, filed Sep. 11, 2015, entitled "Reservoir for Collection and Reuse of Diverted Medium"; which claims priority to and the benefit of U.S. Provisional Application Ser. No. 62/082,260, filed Nov. 20, 2014, entitled "Devices and Methods for Modulating Medium Delivery"; and U.S. Provisional Application Ser. No. 62/048,974, filed Sep. 11, 2014, entitled "Devices and Method for Modulating Medium Delivery." The disclosures of each of these applications are hereby incorporated by reference herein in their entireties.

INTRODUCTION

This disclosure pertains to systems, devices, and methods used to control, transform or otherwise modulate the delivery of a substance, such as radiopaque contrast, to a delivery site and/or systems, devices, and methods that may be used to measure or otherwise make quantitative assessments of a medium delivered to a delivery site. More specifically, it is the intention of the following systems, devices, and methods to modulate and/or assess the delivery of media to a vessel, vascular bed, organ, and/or other corporeal structures so as optimize the delivery of media to the intended site, while reducing inadvertent or excessive introduction of the media to other vessels, vascular beds, organs, and/or other structures, including systemic introduction.

The terms medium (media), agent, substance, material, medicament, and the like, are used generically herein to describe a variety of fluidal materials that may include, at least in part, a substance used in the performance of a diagnostic, therapeutic or/and prophylactic medical procedure and such use is not intended to be limiting.

SUMMARY

This summary is provided to introduce a selection of concepts in a simplified form that are further described below in the Detailed Description. This summary is not intended to identify key features or essential features of the claimed subject matter, is not intended to describe each disclosed embodiment or every implementation of the claimed subject matter, and is not intended to be used as an aid in determining the scope of the claimed subject matter. Many other novel advantages, features, and relationships will become apparent as this description proceeds. The figures and the description that follow more particularly exemplify illustrative embodiments.

In one aspect, the technology relates to an apparatus having: a syringe housing; a plunger having a shaft, wherein the plunger is slidably received within the syringe housing between a first position and a second position; at least one Hall sensor disposed within the shaft; and at least one magnet fixed proximate the syringe housing. In an embodiment, the magnet includes a plurality of magnets disposed about the syringe housing. In another embodiment, a magnet retention ring is disposed about the syringe housing, wherein the plurality of magnets are disposed within the magnet retention ring. In yet another embodiment, the Hall sensor includes a plurality of Hall sensors. In still another embodiment, the shaft defines an interior chamber and the plurality of Hall sensors are disposed linearly within the chamber.

In another embodiment of the above aspect, a wireless transmitter is disposed within the chamber. In an embodiment, the apparatus further has a circuit board, wherein the plurality of Hall sensors are disposed on the circuit board; a battery is disposed on the circuit board, wherein the battery is configured to provide power to at least one of the plurality of Hall sensors; and a switch is disposed on the circuit board for selectively connecting power between the battery and the at least one of the plurality of Hall sensors. In another embodiment, the switch is activated based on a movement of the plunger.

In another aspect, the technology relates to an apparatus having: a syringe housing defining an axis; a plunger slidably disposed along the axis within the syringe housing; a plurality of Hall sensors disposed along the plunger; at least one magnet fixed relative to the axis, such that a movement of the plunger along the axis moves at least one of the plurality of Hall sensors through a magnetic field created by the at least one magnet. In an embodiment, the at least one magnet includes a plurality of magnets disposed about the axis, so as to create a substantially circular magnetic field. In another embodiment, the apparatus further has a magnet retention ring disposed about the syringe housing and wherein the plurality of magnets are disposed within the magnet retention ring. In yet another embodiment, a wireless transmitter is disposed within the plunger. In still another embodiment, a battery is disposed within the plunger, wherein the battery is configured to provide power to the wireless transmitter and at least one of the plurality of Hall sensors; and a switch disposed within the plunger for selectively connecting power between the battery and the wireless transmitter and at least one of the plurality of Hall sensors.

In another embodiment of the above aspect, the switch is activated based on a movement of the plunger. In an embodiment, the switch includes a reed switch. In another embodiment, the plunger is configured for rotational movement about the axis, and wherein the at least one of the plurality of Hall sensors is disposed so as to pass through the magnetic field at any angular position of the plunger about the axis. In yet another embodiment, the magnet retention ring is disposed proximate a proximal end of the syringe housing. In still another embodiment, the magnet is secured directly to the syringe housing.

In another aspect, the technology relates to a method of determining a condition of a syringe having a syringe housing and a plunger slidably disposed in the syringe housing, the method including receiving a first signal from a first Hall sensor, wherein a position of the first Hall sensor on the plunger is known. In an embodiment, method further includes determining a second position of the plunger based at least in part on a received second signal.

Further, in another aspect, the technology relates to a system for modulating a fluid being delivered to a patient and the ability to measure the amount delivered. A myriad of ways of measuring a volume in a chamber, and the subsequent amount of medium injected to a site in a patient, are described. Further, the ability to modulate the delivery of a medium to a patient is exemplarily described. The modulation in one aspect may include diversion of a portion of medium being injected by a syringe (or the like). An aspect of the technology relates to measurement of a total amount of medium ejected from a syringe/chamber, while measuring an amount of medium diverted away from the patient into a "diversion" reservoir, so as to determine the actual volume delivered to an intended site in the patient.

In another aspect, the technology relates to a method of determining an amount of medium injected into a patient, the method including: receiving an injection signal from a sensor associated with an injection syringe; receiving a diversion signal from a sensor associated with a diversion reservoir; and determining the amount of medium injected based at least in part on the injection signal and the diversion signal. In an embodiment, the method includes sending a signal associated with the amount of medium injected. In another embodiment, the method includes displaying the amount of medium injected. In yet another embodiment, the method includes receiving a flush signal associated with a valve of a saline flush system. In still another embodiment, the method includes disregarding at least one of the injection signal and the diversion signal based at least in part on the flush signal. In another embodiment, the method includes adjusting a position of at least one valve based at least in part on the flush signal.

BRIEF DESCRIPTION OF THE DRAWINGS

There are shown in the drawings, embodiments which are presently preferred, it being understood, however, that the technology is not limited to the precise arrangements and instrumentalities shown.

FIGS. 5A-5C depict embodiments of a monitoring syringe.

FIG. 15A is a perspective view of another example of a medium diversion reservoir.

FIG. 15B is a perspective exploded view of the medium diversion reservoir of FIG. 15A.

DETAILED DESCRIPTION

Figure 1A:
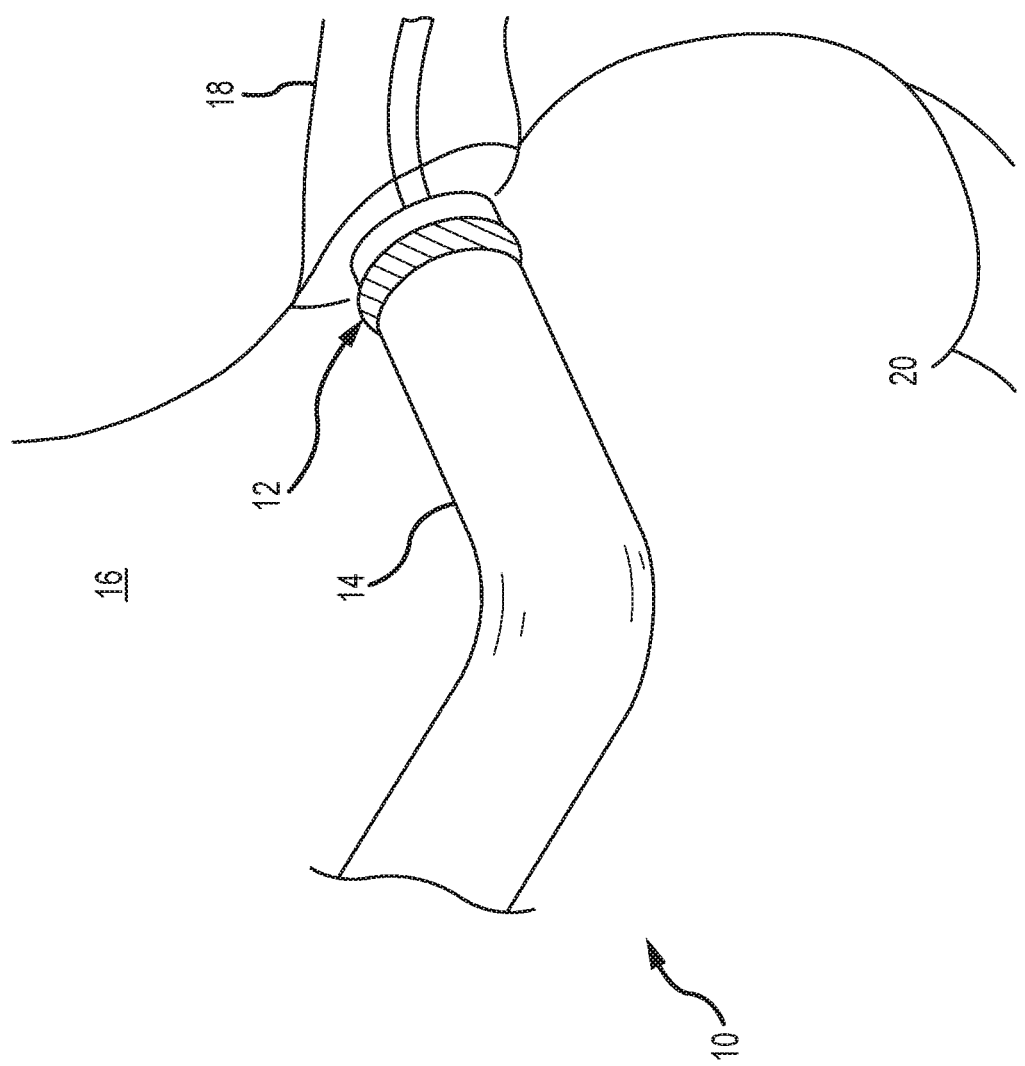
FIG. 1A depicts an exemplary synchronized agent delivery with indirect modulation, adjacent a distal portion of a treatment system therefor.

There are numerous occasions in the diagnostic, prophylactic and treatment practice of medicine wherein an agent, medicant, or medium is preferably delivered to a specific site within the body, as opposed to a more general, systemic introduction. One such exemplary occasion is the delivery of contrast media to coronary vasculature in the diagnosis (i.e., angiography) and treatment (i.e., balloon angioplasty and stenting) of coronary vascular disease. The description, as well as the devices and methods described herein, may be used in modulating and/or monitoring medium delivery to the coronary vasculature in prevention of toxic systemic effects of such an agent. One skilled in the art, however, would recognize that there are many other applications wherein the controlled delivery and/or quantitative assessment of a media to a specific vessel, structure, organ or site of the body may also benefit from the devices and methods disclosed herein. For simplicity, these devices and methods may be described as they relate to contrast media delivery modulation and/or measurement. As such, they may be used in the prevention of Contrast Induced Nephropathy; however, it is not intended, nor should it be construed, so as to limit the use to this sole purpose. Exemplary other uses may include the delivery, injection, modulation, or measurement of: cancer treatment agent to a tumor, thrombolytic to an occluded artery, occluding or sclerosing agent to a vascular malformation or diseased tissue; genetic agent to a muscular bed, neural cavity or organ, emulsion to the eye, bulking agent to musculature and/or sphincter, imaging agent to the lymphatic system, antibiotics to an infected tissue, supplements in the dialysis of the kidney, to name but a few.

EXAMPLE

Prevention of Contrast Induced Nephropathy

Contrast Induced Nephropathy (CIN) is a form of kidney damage caused by the toxic effects of dyes (radiopaque contrast media) used, for example, by cardiologists to image the heart and its blood vessels during commonly performed heart procedures, such as angiography, angioplasty, and stenting. In general, the dye is toxic and is known to damage kidneys. Although most healthy patients tolerate some amount of the "toxicity," patients with poorly or non-functioning kidneys may suffer from rapidly declining health, poor quality of life, and significantly shortened life expectancy. Potential consequences of CIN include: irreversible damage to the kidneys, longer hospital stays, increased risk of heart disease, increased risk of long-term dialysis, and ultimately, a higher mortality risk. For patients who acquire CIN, their risk of dying remains higher than others without CIN, and this risk can continue up to five years after their procedure. CIN has a significant economic burden on the healthcare system and currently there is no treatment available to reverse damage to the kidneys or improper kidney performance, once a patient develops CIN.

To date, there have been attempts in reducing the toxic effects of contrast media on patients who undergo procedures involving dyes, especially those patients who are at high risk for developing CIN. Some of these efforts have been to: change the inherent toxicity (of a chemical or molecular nature) of the dyes, reduce the total amount of contrast agent injected (through injection management and/or dye concentration), and remove media through coronary vasculature isolation and blood/contrast agent collection systems, to name a few. These methods and devices used in the control of the toxic effects of contrast agents have had their inherent compromises in effectively delivering a contrast media specifically to a target site while minimizing the systemic effects. As an example, changing the composition of a dye and/or injection concentration may help reduce a contrast agent's inherent toxicity at the expense of the contrast agent's ability to perform its intended function (e.g., visualization of vasculature). Conversely, the ability to "collect" contrast agent laden blood "downstream" from the visualization site may ensure visualization, but requires the complexity of placement and operation of a collection system.

Other attempts to manage the amount of contrast agent delivered to a patient have employed automated, powered (versus manual, syringe-injected) contrast media injection systems. Close monitoring and control of the total quantity of contrast agent injected may have a positive impact in reducing the incidence of CIN. However, these injection systems are expensive (including capital equipment and disposables), cumbersome to use within a cath lab, and take additional time and expertise to set up and operate properly. Improper use could negate any benefits seen by better management of the quantity of the contrast agent delivered to a patient, and the additional time required to set up such a system may also add significant complexity to a procedure. The devices and methods described herein may measure or otherwise quantitatively assess the amount of medium injected or delivered to a delivery site using a relatively fast, simple, economical, and safe system.

The measurement systems described herein may be employed as a system of quantitative assessment or in combination with a modulator. Additional systems are described in U.S. patent application Ser. No. 13/839,771, the disclosure of which is hereby incorporated by reference herein in its entirety. FIGS. 1A-1D depict embodiments where a modulator is constructed so as to measure the amount of an agent delivered from the system. Conversely, FIG. 2, for example, describes the use of a measurement system for the quantitative assessment of the volume of medium delivered and the inherent analysis of the total volume delivered versus some predetermined critical amount, such as the Gurm ratio, whether or not it is used with a modulator.

It should be understood that measurements may be performed prior to a medium being modulated, simultaneously with modulation, or after the modulation process, if desired. Further, it is also contemplated that the measurement devices and methods may be used with any of the modulation systems, such as described in U.S. patent application Ser. No. 13/839,771. Moreover, the embodiments described herein are exemplary in nature and should not be construed as limiting the various combinations possible.

Some embodiments of control and modulation devices disclosed herein may send and/or receive a sensor signal so as to coordinate a valving, controlling, or otherwise modulating function on an injection agent before the agent enters an intended target injection site. Modulation may include, for example, valving (or otherwise modulating) an injection dispensed from an injection device. As described in U.S. patent application Ser. No. 13/839,771, indirect valving (or otherwise controlling mechanisms) may be proximally or distally positioned within, about, and/or upon the agent delivery system. An example of an indirect modulation control system 10 is depicted in FIGS. 1A-1D. In this example, a sensor 12 is deployed distally on a delivery catheter 14 (as seen in FIG. 1A) and a modulating device 30 (of FIG. 1B) is provided proximally. The sensor 12 of FIG. 1A is an exemplary pressure sensor positioned on the distal tip of the delivery catheter 14. As described previously, this is only one example of a type of sensor that may be used in obtaining a signal to synchronize the delivery of medium with the blood flow rate. Moreover, FIG. 1A illustrates the positioning of the sensor 12 upon the distal tip of the delivery catheter 14 within the aorta 16 to the left coronary artery 18, off the aortic root 20. The exemplary positioning of the sensor 12 in FIG. 1A should not be limited to that shown in order to perform the functions described herein, since there may be a multitude of sensor types (and commensurate signals) positioned at various locations on (i.e., as a function of respiration), through (i.e., as a function of imaging) and within the body (i.e., as a function of a variable proximate a target delivery site). Clearly, even the placement of a distal pressure sensor in exemplary FIG. 1A could take many forms, such as: a pressure wire alongside the catheter, a lumen within the catheter body for pressure measurement, a pressure sensor deployed within the distal tip of the catheter, and a pressure sensor deployed distally of the distal tip of the catheter and into the target vessel, to name but a few.

Figure 1B:
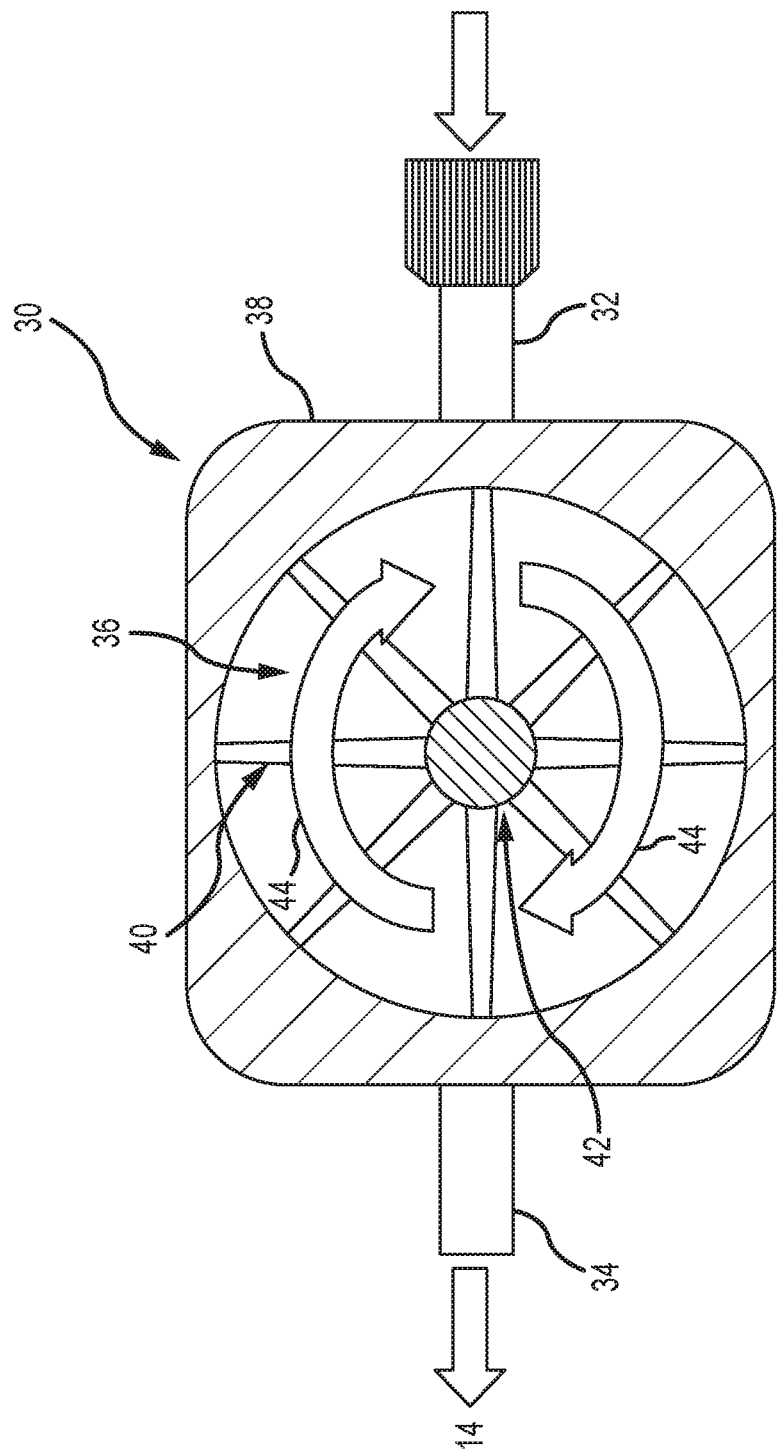
FIG. 1B depicts a top view of an exemplary synchronized agent delivery with indirect modulation, adjacent a proximal portion of such a treatment system.

Referring to FIG. 1B, modulating device 30 may include an inlet port 32 (from the injection device) and an outlet port 34 (to the delivery catheter 14). The flow of injection fluid may pass through the injection port 32 and into a fluid chamber 36 within a body or housing 38 of the modulator 30. The modulator 30 may have a plurality of vane/plates 40 attached to a cylindrical hub 42 disposed within the fluid chamber 36. The vanes 40 and hub 42 may be formed to define a "pinwheel" structure of vane-hub that is capable of rotating freely (relative to fluid chamber 36 and body 38 of modulator 30) upon the injection of medium into the fluid chamber 36 through the injection port 32. The hub 42 may be designed to preferentially rotate in one direction. For example, FIG. 1B illustrates the preferential flow of fluid and rotation of the vane-hub, in a clockwise direction, via flow arrows 44. From the fluid chamber 36, injection fluid may flow out of the modulator 30 via the outlet port 34.

One advantage of the vane-hub modulator 30 depicted in FIG. 1B is that it may be easy to measure, or otherwise identify, the total volume of injection fluid delivered through the modulating device 30 (over time) since the volume of fluid passing through the device 30 during one rotation of the vane 40 or hub 42 may be easily determined, and the number of rotations simply counted by a counting mechanism. Alternatively, each "cell" of fluid between adjacent vanes 40 may be readily counted by a counting mechanism. The counting mechanism may include a magnetic, mechanical, ultrasonic, infrared or similar measurement device capable of identifying the number of times a vane 40 and/or some other element of the device 30 has passed within its field of measurement, or by determining the number of times the axis of the hub 42 has rotated. The output of such a counting mechanism may be utilized to determine and display (in real time) the total volume of medium used during a procedure. Advantageously, in the management of medium injected, an operator or physician may readily see the amount of medium used (as determined by the counting mechanism and presented by a suitable display or indicative output). The determination of the volume (via calculations or conversions based on, for example, counted rotations) may be performed as part of the counting device, or may be performed by a display device. In addition to providing volume measurements, the counting mechanism, signal, or display may incorporate various algorithms to alert the operator before or when maximum volume of agent has been administered (based upon an operator-determined value, Maximum Acceptable Contrast Dose, Gurm ratio, etc.). For example, the Maximum Acceptable Contrast Dose index, as described by Cigarroa, et al. (June 1989) "Dosing of Contrast Material to Prevent Nephropathy in Patients with Renal Disease" Am Jour of Med. 649-652, suggests that a maximum amount of contrast injected (in mL) be equal to 5 ml×body weight (Kg)/Baseline Serum Creatinine level (in mg/dL). In another example, the maximum amount of contrast injected (in mL) as described in Gurm, et al. "Renal Function-Based Dosing to Define Safe Limits of Radiographic Contrast Media in Patients Undergoing Percutaneous Coronary Interventions" JACC 2011:58:907-14, suggests that the maximum contrast used (in mL) should be less than, or equal to, 2 if it is divided by a calculated Creatinine Clearance (mL/min) of the patient. Regardless of the indicator utilized, the system may include a display that not only provides total volume used, but also warns the operator of use as compared to one or more indicators of a maximum administration.

Figure 1C:
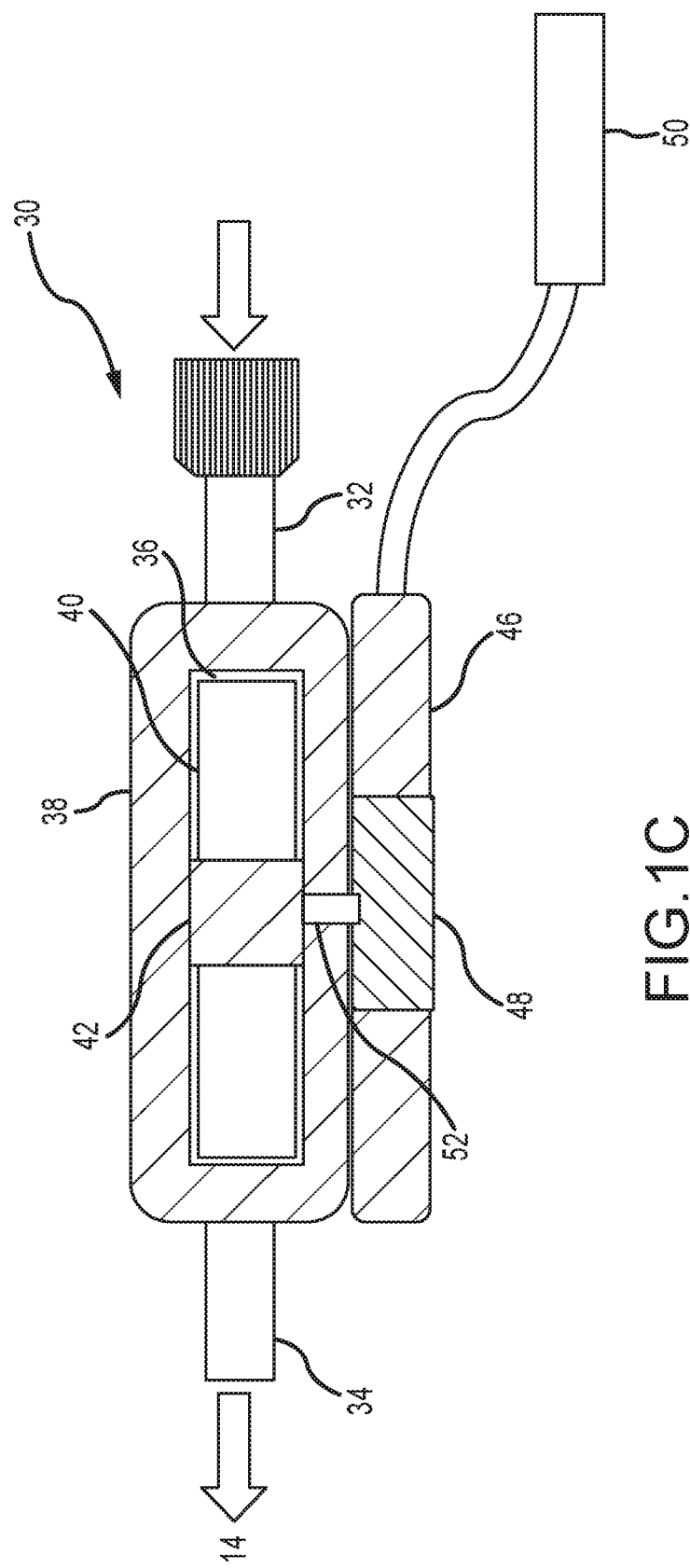
FIG. 1C depicts a side view of an exemplary synchronized agent delivery with indirect modulation, adjacent a proximal portion of such a treatment system.
Figure 1D:
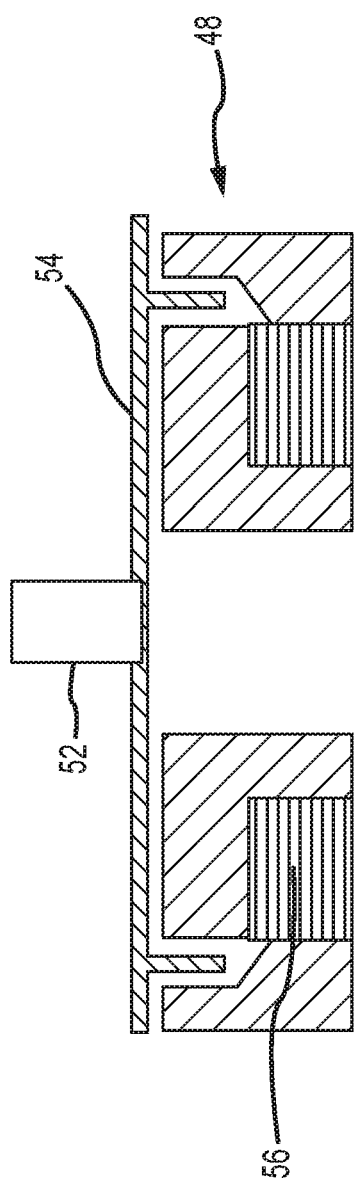
FIG. 1D depicts a side sectional view of the brake mechanism of the exemplary synchronized agent delivery arrangement of FIG. 1C.

Continuing with the description of the exemplary modulation device 30 shown in FIGS. 1B-1C, the vane-hub modulator 30 may include two components. The first, the body 38 (described above) may be situated adjacent a controller/actuator 46 and may include the input port 32, the output port 34 and the fluid chamber 36 with rotating vane 40 and hub 42. The body 38 may come into contact with bodily fluids and, accordingly, may be disposable. The controller/actuator 46 may also include a brake mechanism 48, sensor signal, receiver 50, and the like may be used to clutch, brake, or otherwise inhibit the rotation of the hub 42 so as to provide resistance to rotation. The resistance induced to the rotation may be coordinated with a signal from sensor 12 of FIG. 1A, so as to modulate an injection from an injector to improve an agent fluid flow.

The braking, or clutching, of the modulator 30 of FIG. 1C may be performed through a variety of mechanisms, to include, for example, mechanical, hydromechanical, electromechanical, electromagnetic, chemomechanical, etc. FIG. 1C illustrates one such mechanism 48 for braking a shaft 52 of the hub 42, using electromagnetic force. The exemplary braking structure 48 is further detailed in FIG. 1D, wherein the longitudinal shaft 52 of the hub 42 is coupled to a hysteresis plate or disc 54 positioned within a magnetic coil 56. When electricity is applied to the magnetic coil 56, a magnetic flux is transferred to the hysteresis disc 54 (as it passes through the field) causing a magnetic "drag" on the disc 54. The drag, or braking, applied to the hysteresis disc 54 (and thus the shaft 52 of the hub 42) may be increased or decreased with increasing or decreasing voltage applied to the magnetic field to modulate the flow of medium as intended. When electrical current is removed, the connected disc 54 may rotate freely about an axis of shaft 52. Upon modulating, braking mechanism 48 of FIG. 1D may increase the drag (reduce the flow rate) of the agent as needed to improve the flow profile of the agent or fluid.

FIGS. 1A-AD describe one system to regulate the flow profile and determine the volume of injection agent through a modulator, and as such, are intended to illustrate the modulation monitoring, control, and measurement concepts disclosed herein without limitation. Therefore, this embodiment is but one example how one might use a modulator device and a measurement device to control the delivery of an agent, as well as measure the amount of agent delivered.

Other embodiments including devices and methods in quantitative assessment, or otherwise measurement, of the volume of delivery of an agent are described below. It is to be understood that these measurement devices may also be used in combination with a variety of agent modulators and the description is intended to be exemplary and not limiting.

Figure 2:
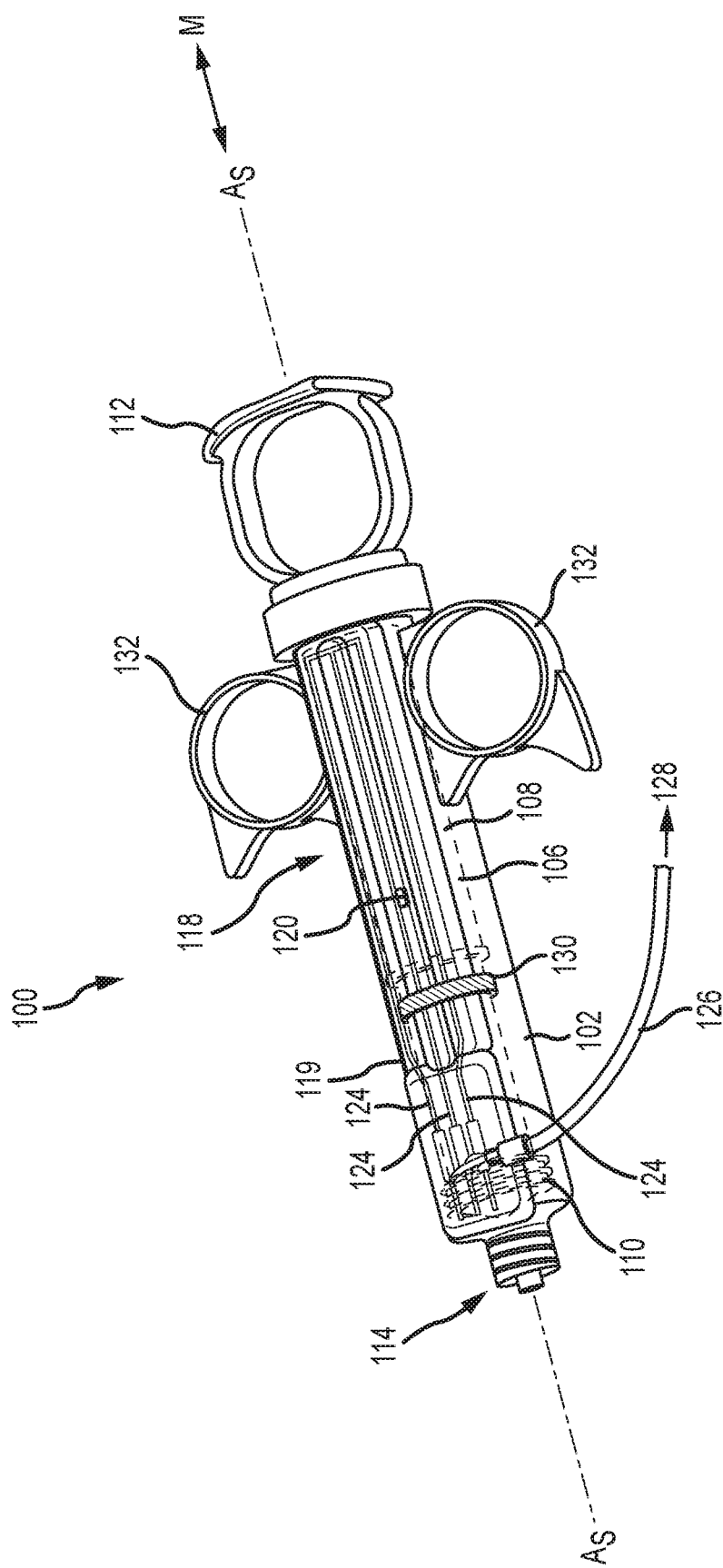
FIG. 2 depicts a perspective view of an embodiment of a monitoring syringe.
Figure 3:
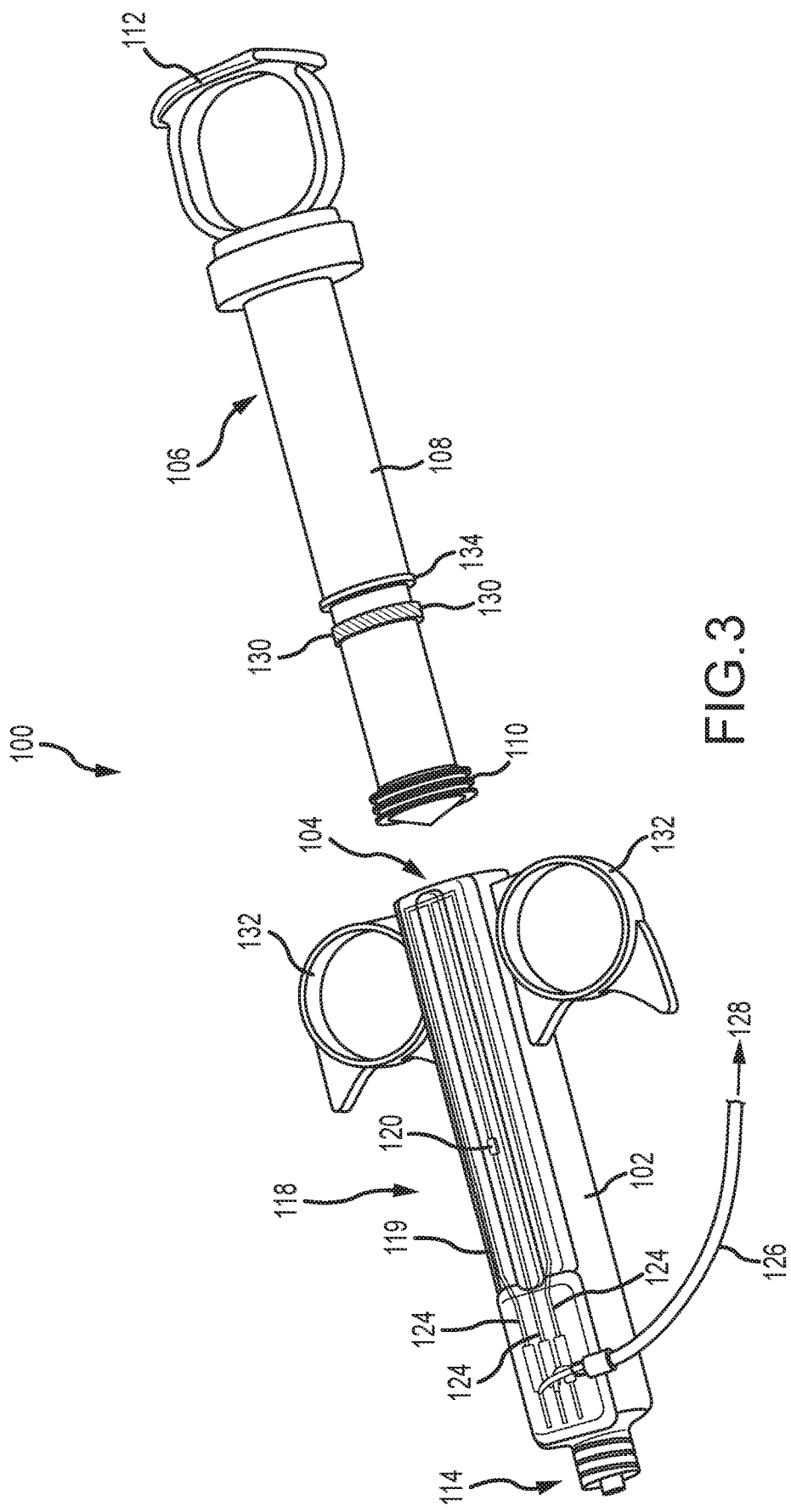
FIG. 3 depicts a partially exploded perspective view of the monitoring syringe of FIG. 2.

FIGS. 2 and 3 depict a perspective view and a perspective exploded view, respectively, of a monitoring syringe 100. The monitoring syringe 100 includes a syringe housing 102 (or chamber) defining an inner bore 104. A plunger 106 including a shaft 108 and a piston 110 is slidably received in the bore 104. More specifically, the piston 110 is slidably engaged with an interior surface of the bore 104 and linear movement M of the shaft 108 within the bore 104 moves the piston 110. Movement M is along the syringe axis $A_S$. The plunger 106 is moved back and forth within the bore 104 by the movement of a thumb pad, such as a thumb-ring 112, as described in more detail below. As the plunger 106 is moved M in a direction towards the discharge end 114 of the syringe housing 102, the fluid contained therein is discharged into a tube or needle (not shown) and delivered to a patient. Note that throughout the description a cylindrical-type chamber 102 and inner bore 104 are described; however, it is contemplated that there may be a variety of constructions of a housing/bore 102/104 and plunger 106 that provide the function as anticipated herein and the shape (including rectangular, ovular, triangular cross-section, etc.), in and of itself, should not be limiting.

In the depicted embodiment, a light sensor module 118 is secured to an exterior surface of the syringe housing 102. The light sensor module 118 includes a light sensor housing 119 that encloses a light sensor 120. In certain embodiments, the light sensor 120 may be a linear array comprising a plurality of pixels, such as model no. TSL1406R manufactured by AMS-TAOS USA, Inc., of Plano, Tex. In other embodiments, the light sensor 120 may be one or more discrete light sensors, such as photoresistors. In general, a greater number of discrete light sensor elements (pixels, photoresistors, or otherwise), may improve accuracy. One or more leads or wires 124 extend from an end of the light sensor module 118, as required or desired for a particular application. However, one skilled in the art would readily recognize that wires 124 need not be utilized with different sensor configurations. For example, using a light sensor on a circuit board may require alternative connections. A cable 126 connects at an end 128 to an interface unit that analyzes the output of the light sensor module 118 and provides this information to a user of the monitoring syringe 100, typically on a display. In other embodiments, communication may be via a radio, Bluetooth, of other wireless connection. The displayed information may include volume of the chamber, volume remaining, volume dispensed, fluid type, flow rate, fluid pressure or temperature and/or other information, as required or desired for a particular application.

In the depicted embodiment, the shaft 108 of the plunger 106 is substantially translucent, meaning light may generally pass through the shaft 108. A discrete portion or band 130 may be disposed on or formed with the shaft 108. The band 130, in this case, is a portion of the shaft 108 having a translucency less than the translucency of the remainder of shaft 108, or an opacity greater than the opacity of the remainder of the shaft. As the plunger 106 is slidingly moved M along the axis $A_s$, the band 130 of lesser transparency passes in front of the light sensor 120 of the light sensor element 118. Light passes through the plunger portion having higher translucency and is received by the light sensor module 118. The light sensor module 118 sends a signal to the interface unit that determines the position of the plunger 106 within the syringe housing 102, based on the opacity of band 130 along the light sensor 120. Thus, the position of the plunger 106 can be determined. The interface may also determine the various types of information listed above, based on a known diameter and length of the bore 104 of the syringe housing 102. Two finger rings or tabs 132 receive the fingers of a user during use. A stop 134 prevents the plunger 106 from being pulled out of the syringe housing 102.

Figure 4A:
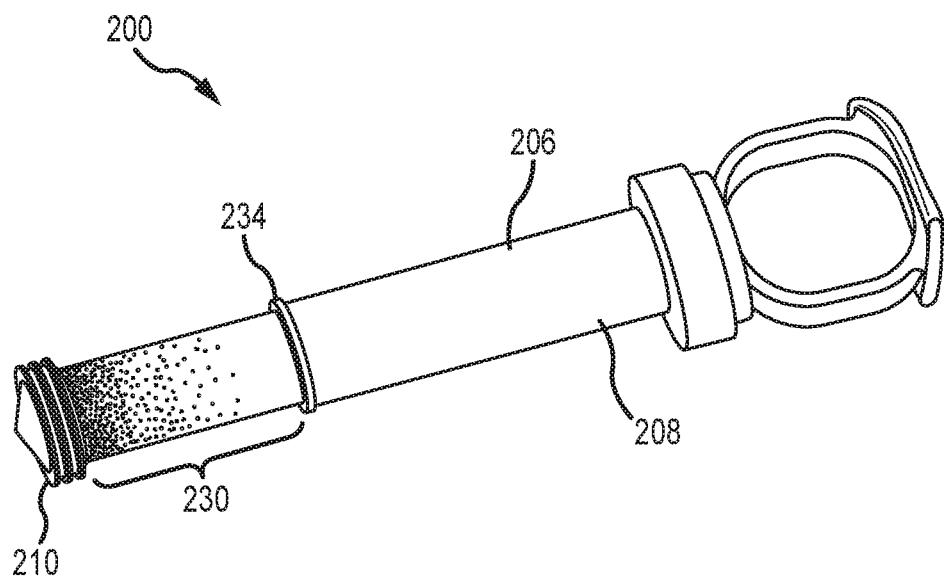
FIGS. 4A-4C depict partial enlarged perspective views of other embodiments of monitoring syringes.
Figure 4B:
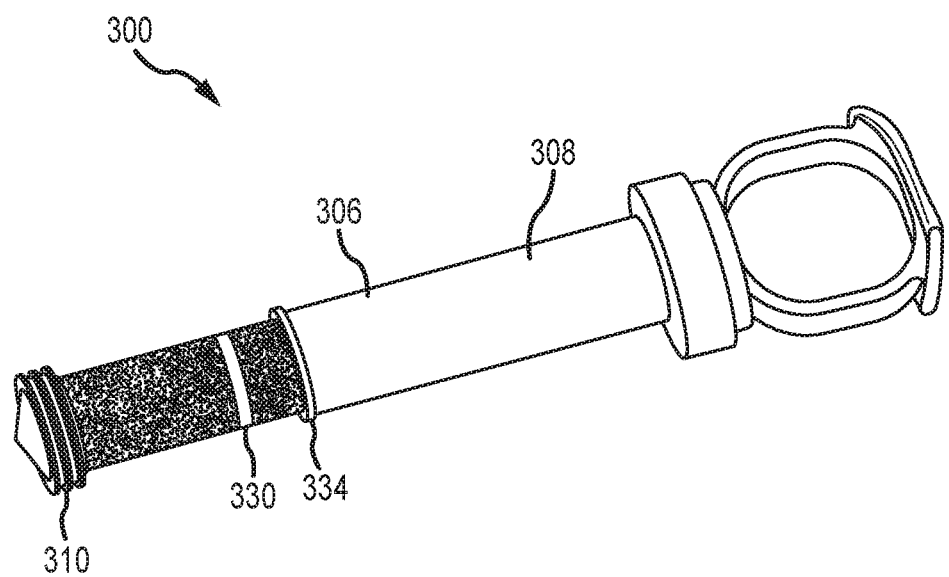
Figure 4C:
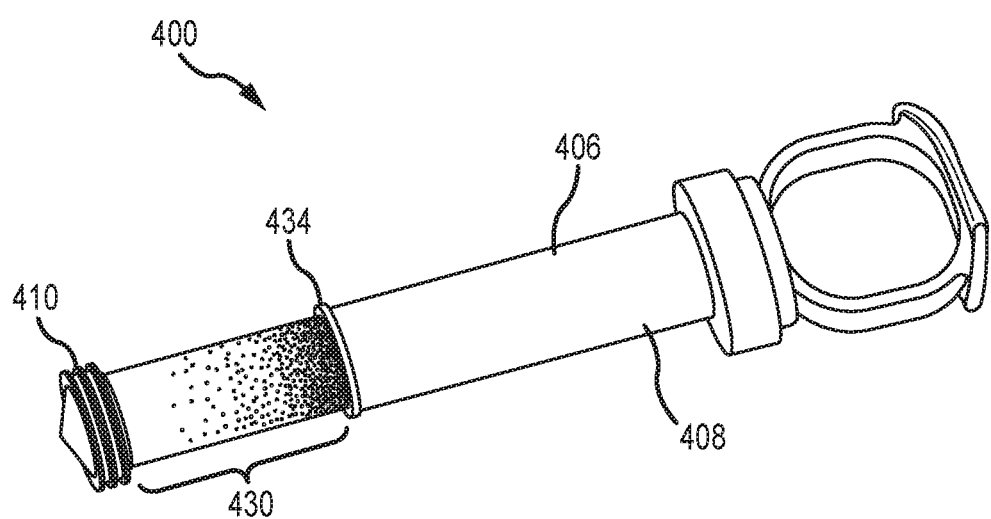

FIGS. 4A-4C depict various alternative configurations of plungers that may be utilized with various monitoring syringes herein. FIG. 4A depicts a partial enlarged perspective view of another embodiment of a monitoring syringe 200. In this embodiment, a plunger 206 includes a shaft 208. Rather than the discrete band depicted above in FIGS. 2 and 3, the depicted embodiment includes a gradation 230 of varying translucency/opacity along the plunger shaft 208. In the depicted embodiment, the gradation 230 is darker (i.e., less translucent or more opaque) proximate the piston 210. Proximate the stop 234, the translucency of the gradation 230 is higher (and conversely, the opacity lower). The transition of the gradation may be smooth or in discrete bands. In certain embodiments such as the one depicted in FIG. 4A, no shading may be present proximate the stop 234 and the translucency of that portion may be the same as that of the shaft 208, generally.

FIG. 4B depicts a partial enlarged perspective view of another embodiment of a monitoring syringe 300. In this embodiment, a plunger 306 includes a shaft 308. Rather than the discrete higher opacity band depicted above in FIGS. 2 and 3, the depicted embodiment utilizes a shaft 308 having a discrete band 330 of higher translucency. That is, the portion of the shaft 330 disposed between the piston 310 and stop 334 is substantially opaque, while the band 330 is substantially translucent.

FIG. 4C depicts a partial enlarged perspective view of another embodiment of a monitoring syringe 400. In this embodiment, a plunger 406 includes a shaft 408. The gradation 430 is disposed opposite the gradation of the embodiment of FIG. 4A. In the embodiment of FIG. 4C, the gradation 430 is darker (i.e., less translucent or more opaque) proximate the stop 434. Proximate the piston 410, the translucency of the gradation 430 is higher. The transition of the gradation 430 may be smooth or in discrete bands. In certain embodiments, no shading may be present proximate the piston 410 and the translucency of that portion may be the same as that of the shaft 408, generally.

Any of the configurations of the plungers depicted in FIG. 2, 3, or 4A-4C may be utilized with the monitoring syringes depicted herein. That is, plungers having discrete bands of opacity or translucency, or plungers having increasing or decreasing gradations (measured from the piston to the stop) may be utilized with syringes utilizing light sensor modules. Regardless of plunger opacity/translucency configuration, the light sensor modules detect changes of light being received as the monitoring syringe is used. Depending on the location of one or more light sensors within the light sensor module, the changes enable an interface device to determine the position of the plunger and, accordingly, the volume and other characteristics or conditions of the device.

The various embodiments of measuring syringes of FIGS. 2-4C describe devices that generally include a light sensor module and/or light sensor positioned on, in, or proximate the device housing or bore. The portion of the device including the variation of translucency is principally positioned on, in, or proximate the device plunger. Of course, the configuration of the components can be reversed if desired, such that the housing/bore includes variations in translucency, while the plunger includes a light sensor or light sensor module. These embodiments are also considered within the scope of the technology.

Figure 5C:
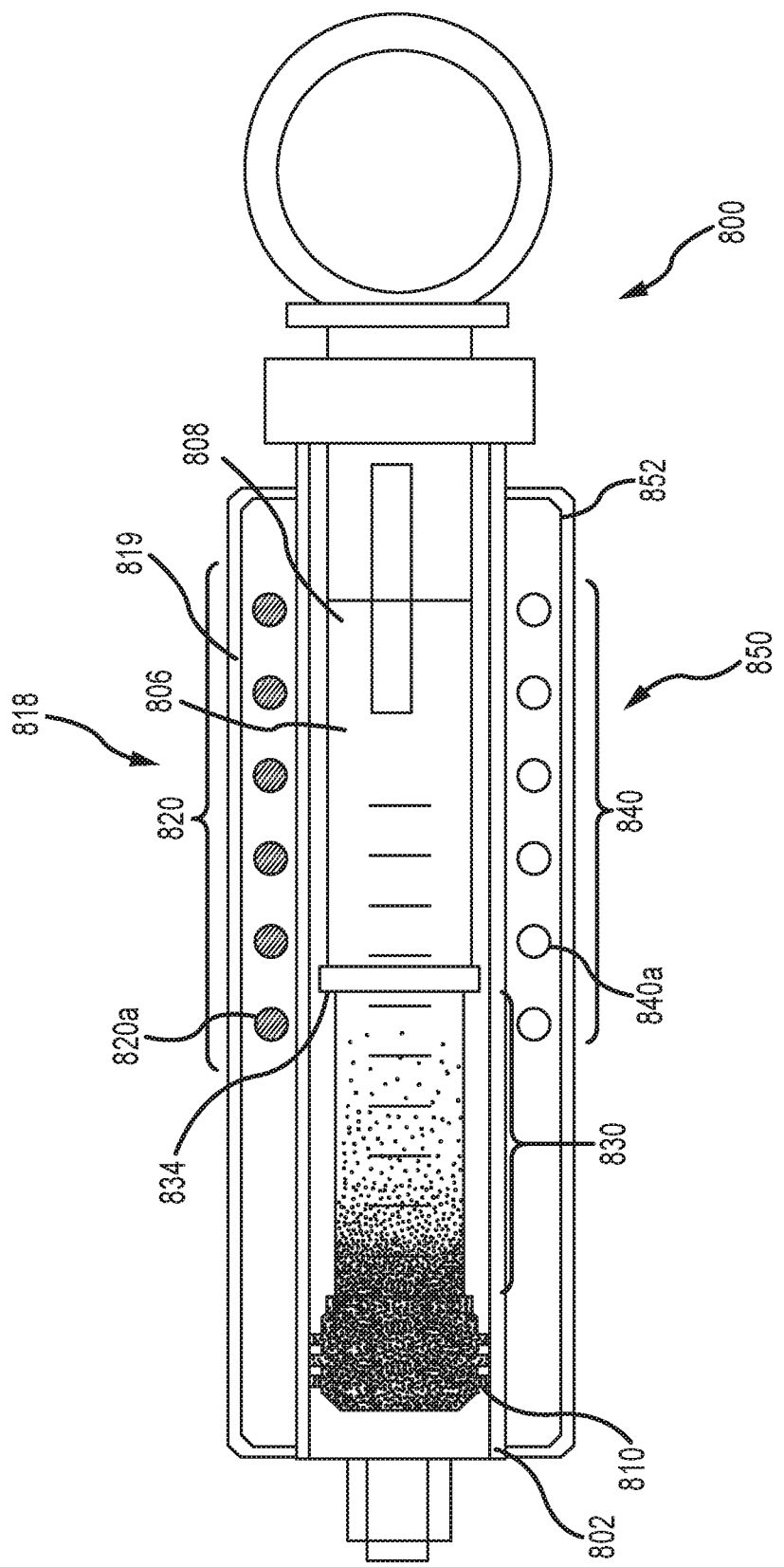

FIGS. 5A-5C depict various embodiments of monitoring syringes. FIG. 5A depicts a monitoring syringe 600 utilizing a sensor module 618. The sensor module 618 includes a sensor housing 619 and a linear array 620. The linear array 620 includes a plurality of pixels 620a. In the depicted embodiment, the monitoring syringe 600 includes a plunger 606 having a shaft 608 including a translucent band 630. The band 630 need not be completely translucent, but merely sufficiently translucent such that the pixels 620a within the light array 620 may detect a change in light received. In this embodiment, the received light is ambient light 640 that may be present in a room such as a surgical suite. Conversely, light source 640 may be from a source other than ambient light, such as an infrared or ultraviolet light generator, for example. Additionally, the light sensor module 618 may be configured with filters to receive light of only a predetermined wavelength (e.g., infrared, ultraviolet, etc.). Alternatively, the plunger 606 or shaft 608 may be configured with a filter to filter the received light to the desired wavelength.

FIG. 5B depicts a monitoring syringe 700 utilizing a sensor module 718. The sensor module includes a sensor housing 719 and a light sensor 720 that includes discrete light sensor elements 720a, such as for example, photoresistors. In the depicted embodiment, the monitoring syringe 700 includes a plunger 706 having a shaft 708 including a gradation 730, wherein the gradation 730 is less translucent proximate the piston 710 and more translucent proximate the stop 734. Instead of utilizing ambient light as with the previous embodiments, the monitoring syringe of FIG. 5B utilizes a light emitter module 750, such as, for example, light emitting diodes (LEDs). The light emitter module 750 is secured to the syringe housing 702 in a manner similar to the light sensor module 718. The light emitter module 750 includes an emitter housing 752 and a light emitter 740 including a plurality of light emitter elements 740a. In the depicted embodiment, the discrete light emitter elements 740a may be disposed opposite and aligned with the discrete light sensor elements 720a, but this is not required. Additionally, the light emitter elements 740a may be configured to only emit light having a particular wavelength, or the light may be filtered so as to restrict the light that is emitted and/or sensed. As the gradation 730 passes between the light sensor module 718 and the light emitter module 750, light signals are received by the discrete light sensor elements 720a. The light sensor module 718 sends signals to an interface, which processes the signals to determine the position of piston 710. The light sensor module 718 and light emitter module 750 are disposed approximately 180 degrees from each other about the circumference of the syringe housing 702. In other embodiments, the modules 718, 750 may be disposed less than about 180 degrees from each other. In certain embodiments, the modules 718, 750 may be disposed about 90 degrees from each other. If desired, the modules 718, 750 may be contained in a common housing.

FIG. 5C depicts a monitoring sensor 800 utilizing a sensor module 818. The sensor module includes a sensor housing 819 and a light sensor 820 that includes discrete light sensor elements 820a, such as photoresistors. In the depicted embodiment, the monitoring syringe 800 includes a plunger 806 having a shaft 808 including a gradation 830, wherein the gradation 830 is less translucent proximate the piston 810 and more translucent proximate the stop 834. The monitoring syringe 800 utilizes a light emitter module 850. The light emitter module 850 is secured to the syringe housing 802 in a manner similar to the light sensor module 818. The light emitter module 850 includes an emitter housing 852 and a light emitter 840 including a plurality of light emitter elements 840a. Note that the emitter housing 852 and sensor housing 819 may include a structural element (e.g., tape or adhesive) to facilitate fixation of emitters/sensors to the chamber, or may include emitters/sensors being disposed within the chamber wall. In the depicted embodiment, the discrete light emitters 840a are disposed opposite and aligned with the discrete light sensor elements 820a, but this is not required. Additionally, the light emitter elements 840a may be configured to only emit light having a particular wavelength (for example, near infrared light generator), or may be filtered. As the gradation 830 passes between the light emitter module 818 and the light sensor module 850, light signals are received by the discrete light sensor elements 820a. The light sensor module 818 sends signals to an interface, which processes the signals to determine the position of piston 810. The light sensor module 818 and light emitter module 850 are disposed approximately 180 degrees from each other about the circumference of the syringe housing 802. In other embodiments, the modules 818, 850 may be disposed as described above with regard to FIG. 5B. The monitoring syringe 800 of FIG. 5C utilizes a light sensor module 818 and light emitter module 850 having higher sensor and emitter densities than those of FIGS. 5A and 5B. As described above, this may result in greater positional accuracy.

Figure 6:
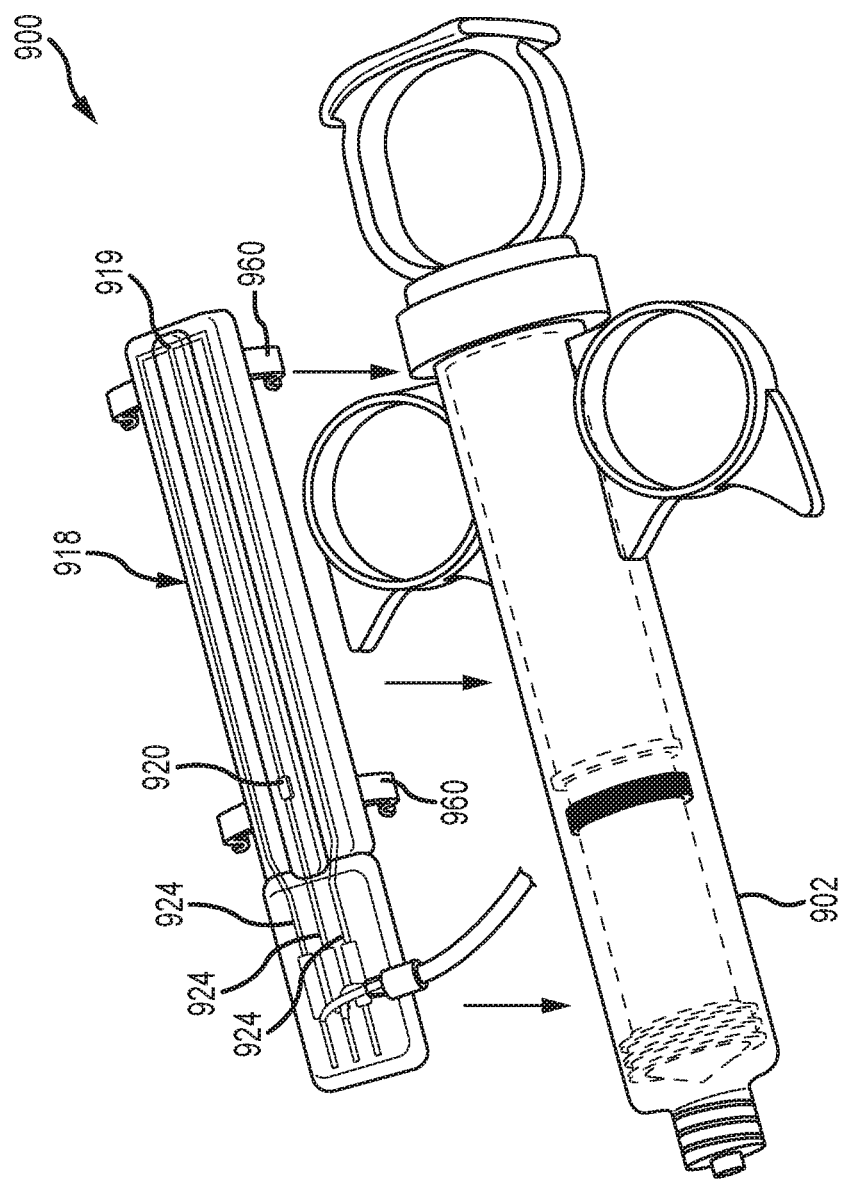
FIG. 6 depicts a partially exploded perspective view of another embodiment of a monitoring syringe.

FIG. 6 depicts another embodiment of a monitoring syringe 900. In this case, the light sensor housing 919, containing the light sensor 920 and wires 924, is detachably secured to the syringe housing 902. The light sensor housing 919 may be secured with clips, C-clamps, resilient catches, or other elements 960 that allow the light sensor housing 919 to be removed from the syringe housing 902. Such a configuration may be desirable so the light sensor housing 919 and related components may be reused on a different syringe, typically after a medical procedure. The light sensor housing 919 may be removed from a first syringe housing 902 and reattached to a second syringe housing at a later time. Once the wires 924 (or similar connective instruments) are reconnected to the interface (as described above) a calibration program may be executed so as to calibrate the light sensor module 918 for the new syringe.

The embodiments described herein may include various elements or components to measure and/or detect a displacement of a plunger within a chamber, such as a syringe. And, with the detection of a positional relationship of a plunger within a chamber, a user may explicitly or implicitly determine a volume of media that may have been ejected from a chamber. Some of the embodiments described may include various sources in the generation of light, as well as components to detect or sense the light, depending on the positional relationship of the plunger/piston and the chamber. Linear encoders, inductive sensors, capacitive touch sensors (with metal actuator in plunger), ultrasonic emitters/receivers, pressure sensors, optical encoders (with fine pitch slots and light source), strain gauges (i.e., to measure weight), electromagnetic emitters/receivers (e.g., navigational systems) are alternative technologies contemplated for the use of measuring an injection delivered from an injector to a patient, with or without measuring a "diversion" reservoir. Other alternative embodiments capable of identifying positional relationships of a plunger and chamber (and changes thereof) may include, without limitation, the following technologies. A Hall sensor (coiled wire along syringe axis) may be placed on, or in proximity to, the chamber with a magnet attached to the plunger (so as to act as a variable proximity sensor). Multiple low sensitivity Hall sensors may be disposed along the chamber of the syringe with a magnet attached to the plunger. Still other embodiments of systems utilizing multiple Hall sensors are described herein. Laser light may be emitted and detected to determine a positional relationship of the plunger along the chamber axis. An absolute encoder may be used to "read" the direct displacement of the plunger.

Figure 9:
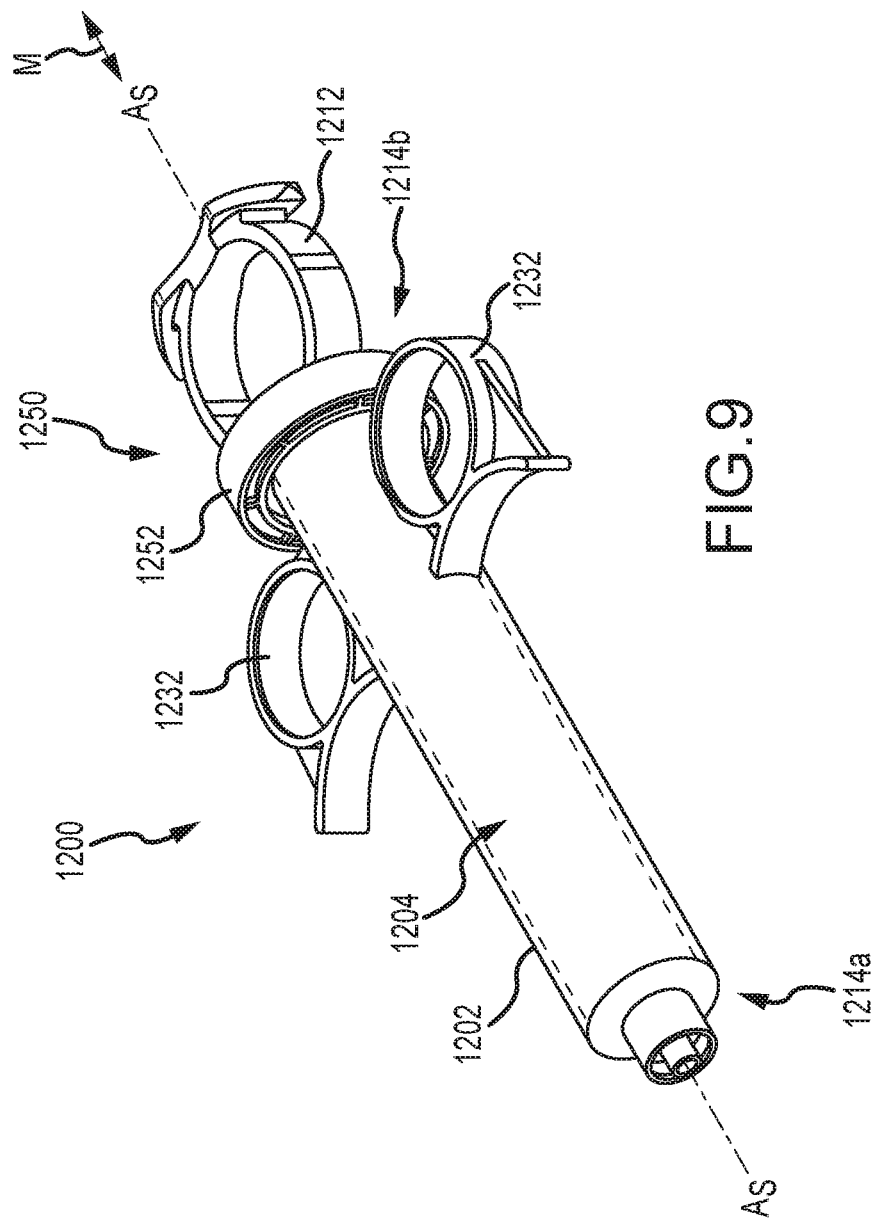
FIG. 9 depicts a perspective view of a first embodiment of a monitoring syringe utilizing a Hall sensor module.

FIG. 9 depicts a perspective view of an embodiment of a monitoring syringe 1200 utilizing a Hall sensor module, which is described in more detail below. The monitoring syringe 1200 includes a syringe housing 1202 defining an inner bore 1204. A plunger or piston, which is described in more detail below, is slidably received in the bore 1204. More specifically, the piston is slidably engaged with an interior surface of the bore 1204 and linear movement M of a plunger shaft within the bore 1204 moves the piston. Movement M is along the syringe axis $A_S$. A thumb ring 1212 may be utilized to push and pull the plunger along axis $A_S$, as described in more detail below. As the plunger is moved M in a direction towards the discharge end 1214a of the syringe housing 1202, the fluid (e.g., media) contained therein is discharged into a tube or needle (not shown) and delivered to a patient. Two finger rings or tabs 1232 receive the fingers of a user during use. Note that throughout the description a cylindrical-type housing 1202 and inner bore 1204 are described; however, it is contemplated that there may be a variety of constructions of a housing/bore 1202/1204 and plunger that provide the function as anticipated herein and the shape (including rectangular, ovular, triangular cross-section, etc.), in and of itself, should not be limiting. The monitoring syringe 1200 also includes a Hall sensor module 1250, described in more detail below. One component of the Hall sensor module 1250 is a magnet retention ring 1252, which is disposed on an outer or exterior surface of the syringe housing 1202. In the depicted embodiment, the magnetic retention ring 1252 is disposed proximate a proximal end 1214b of the housing 1202, but it may be disposed in other locations along the housing 1202.

Figure 10:
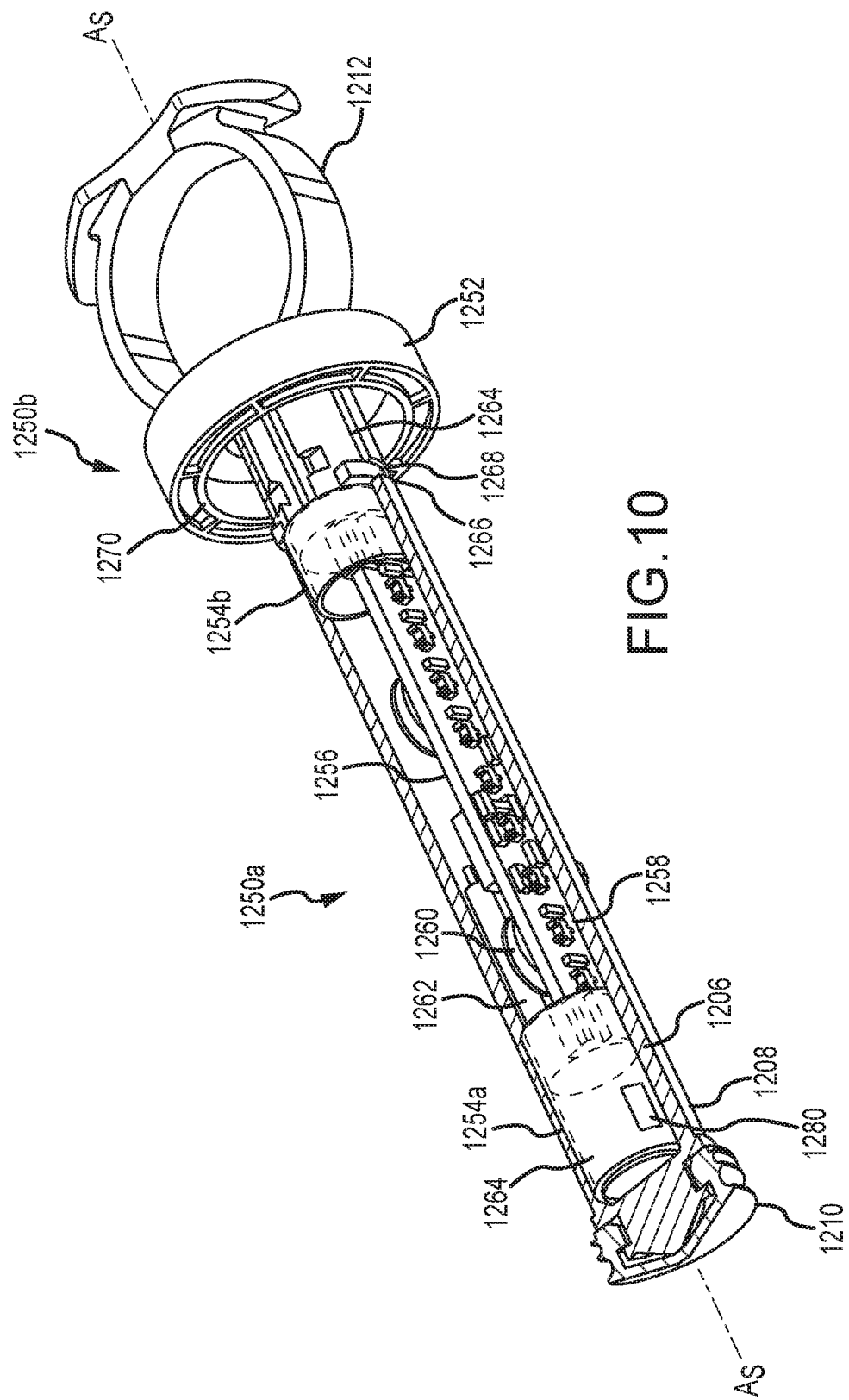
FIG. 10 depicts a partial perspective sectional view of the monitoring syringe of FIG. 9, depicting the Hall sensor module.

FIG. 10 depicts a partial perspective sectional view of the monitoring syringe 1200 of FIG. 9, depicting the Hall sensor module 1250. Certain components 1250a of the Hall sensor module 1250 are disposed within an inner chamber of a hollow shaft 1208 of the plunger 1206, while certain components 1250b are disposed on an exterior surface of the syringe housing. These various components 1250a, 1250b are described in more detail below. So-called internal components 1250a (i.e., internal to the plunger 1206) include retention inserts 1254a, 1254b, a base or circuit board 1256, and a plurality of Hall sensors 1258 disposed thereon. One or more batteries 1260 and a control switch 1262 may also be secured to the circuit board 1256. Signals from the Hall sensors 1258 may be first processed by the circuit board 1256, which may determine the position of the plunger 1206, the volume of media in the syringe, etc., and then send this information to an associated system via the transmitter 1280 for further analysis, display to a doctor, etc. In another embodiment, e.g., if a non-processing base 1256 is used, the signals from each Hall sensor 1258 may be sent directly via the transmitter 1280 to an associated system for processing.

The distal retention insert 1254a may be inserted into the shaft 1208 so as to be near the piston 1210. The distal retention insert 1254a may define a void 1264, which may contain a wireless transmitter 1280, such as a Bluetooth transmitter. The transmitter 1280 may send signals from the Hall sensors 1258 to an associated signal processing device such as described herein. In an alternative embodiment, a cable connection such as described above, may be utilized. The proximal retention insert 1254b is disposed in the hollow shaft 1208 near the thumb ring 1212. Together, the distal retention insert 1254a and the proximal retention insert 1254b support, protect, and retain the circuit board 1256 within the hollow shaft 1208. These two components may be configured for a snug fit in the shaft 1208, or may include a key or other projection to engage with an opening or slot in the shaft 1208, so as to prevent rotation. The retention inserts 1254a, 1254b may be permanently fixed within the shaft 1208, although configuring the inserts 1254a, 1254b for removal may be advantageous so as to allow for replacement or repair of the circuit board 1256, batteries 1260, etc. In one embodiment, the thumb ring 1212 may include a resilient base 1264 including a plurality of projections 1266 that may be engageable with mating slots 1268 in the shaft 1208. Disengaging these projections 1266 allows for removal of the retention inserts 1254a, 1254b and other internal components. A plurality of Hall sensors 1258 are depicted. A greater or fewer number of sensors 1258 may be utilized in various embodiments, although a greater number of sensors 1258 may provide for more accurate determinations with regard the position of the plunger 1206. The Hall sensors 1258 are disposed linearly within the chamber so as to be substantially aligned with, or parallel to, the axis $A_S$.

External components 1250b include the magnet retention ring 1252, which holds a plurality of magnets 1270, which are arc magnets, in the depicted embodiment. In other embodiments, cube, cylindrical, or other magnets may be utilized. The positions of the magnets 1270 are fixed relative to and about the syringe housing. The arc magnets 1270 form a substantially circular magnetic field through which the shaft 1208 (and the Hall sensors 1258) pass when the shaft 1208 is withdrawn from or inserted into the inner bore of the syringe. The circular magnetic field enables the Hall sensors 1258 to detect the field, regardless of the rotational position of the plunger 1206 about the axis $A_S$. In other embodiments, the magnets 1270 may be secured directly to the syringe housing without the magnet retention ring.

Figure 11:
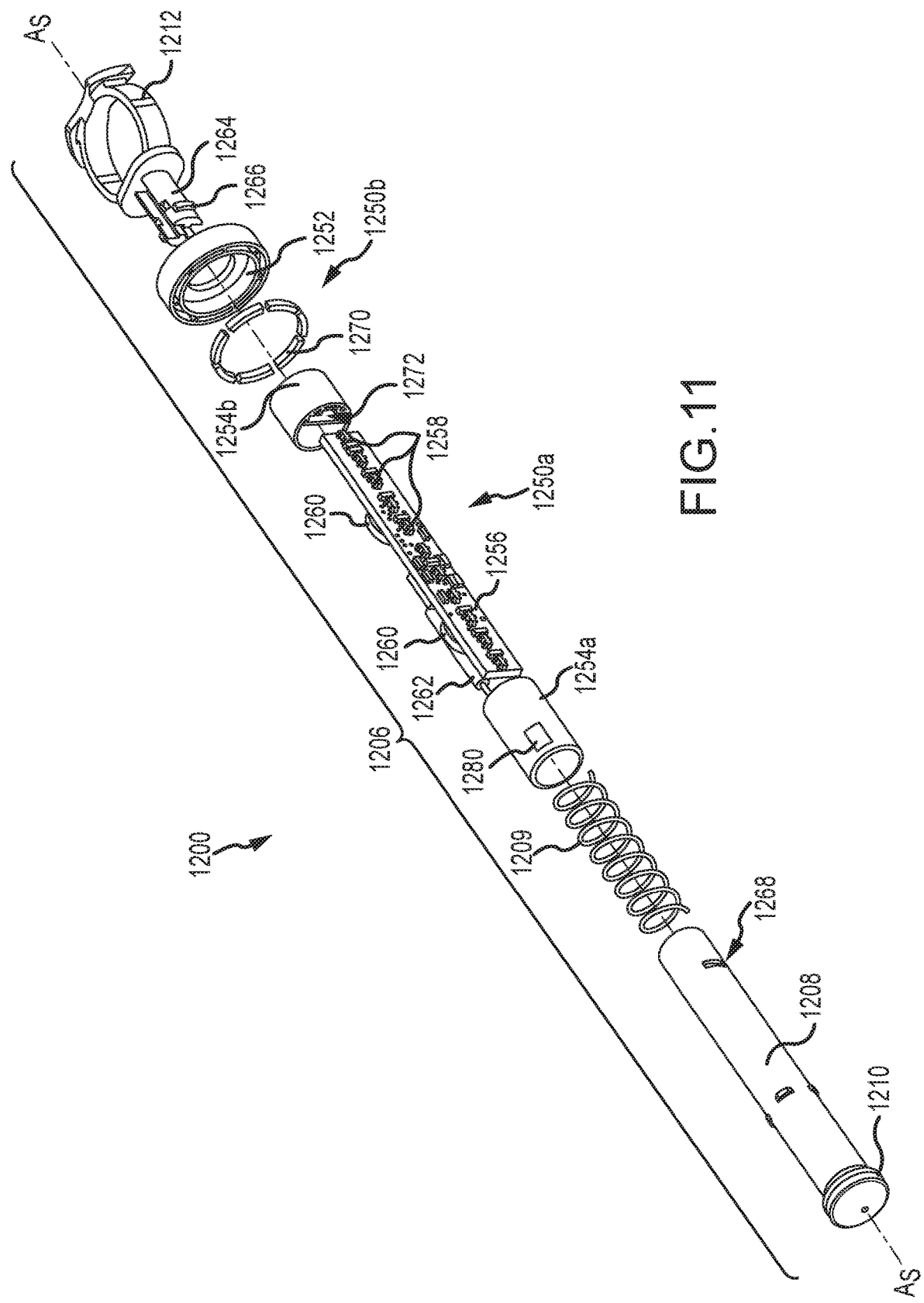
FIG. 11 depicts a partial exploded perspective view of the monitoring syringe of FIG. 10.
Figure 12:
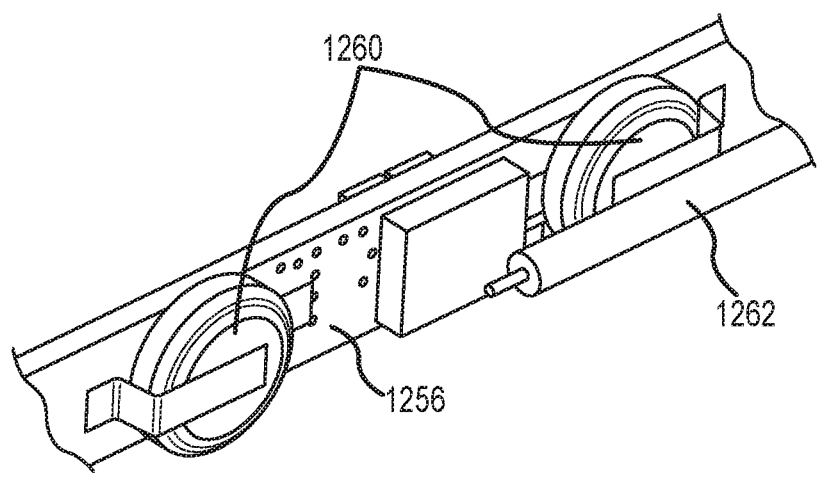
FIG. 12 depicts a partial perspective view of a Hall sensor module.

FIG. 11 depicts a partial exploded perspective view of a portion of the monitoring syringe 1200, as seen in FIG. 10. More specifically, the plunger 1206, Hall sensor module internal components 1250a, and Hall sensor module external components 1250b are depicted. In general, certain of these components are described above in FIGS. 9-10 and are not necessarily described further. In the depicted embodiment, however, both the distal retention insert 1254a and proximal retention insert 1254b include shaped recesses 1272 that are configured to receive the circuit board 1256 so as to hold that element in place. The recesses 1272 are disposed in the inserts 1254a, 1254b so as to conserve space within the hollow shaft 1208 of the plunger 1206. On a side of the circuit board 1256 opposite the Hall sensors 1258 are disposed a plurality of batteries 1260. This is also depicted in FIG. 12. Additionally, a switch 1262 may be disposed proximate the batteries 1260 or elsewhere within the hollow shaft 1208. The switch 1262, in certain embodiments, may be a reed switch that detects plunger movement and moves to an engaged or activated position. The switch 1262 is not required but may help preserve power when the syringe 1200 is not in use. When activated, the switch 1262 selectively connects power from the batteries 1260 to either or both of the plurality of Hall sensors 1258 and the wireless transmitter 1280. In other embodiments, a manually-operated switched, such as a pull tab, button, or rocker switch may be actuated by the user.

In a further embodiment of a system, the measurement components of a monitoring syringe 1200 could also be utilized to measure a volume of medium diverted by a modulator to a medium diversion reservoir, in systems that employ a reservoir in the introduction of contrast to a patient. Such medium diversion reservoirs, and their incorporation into related medium management and monitoring systems, are described elsewhere herein. In such cases, the inner bone 1204 may form a fluid reservoir to capture medium that may diverted by a modulator away from the injection of medium to the delivery catheter. In an additional embodiment of a reservoir, the chamber may be sufficiently pressurized by a force acting upon the plunger 1206 to facilitate controlled filling, release and measurement of a medium within the chamber. The force may bias the piston 1210 into the fluid contained in the bore 1204, while the Hall sensors 1258 continue to detect a position of the plunger 1206. In the depicted example, to configure the monitoring syringe 1200 as a pressurized diversion reservoir, a spring 1209 may be disposed about the hollow shaft 1208 of the plunger 1206. This spring 1209 biases the piston 1210 towards the discharge end 1214a of the syringe housing 1202. Other spring configurations and/or biasing mechanisms may be utilized, wherein they may be generally disposed about the syringe axis $A_s$ so as to provide for a balanced application of force.

Figure 13:
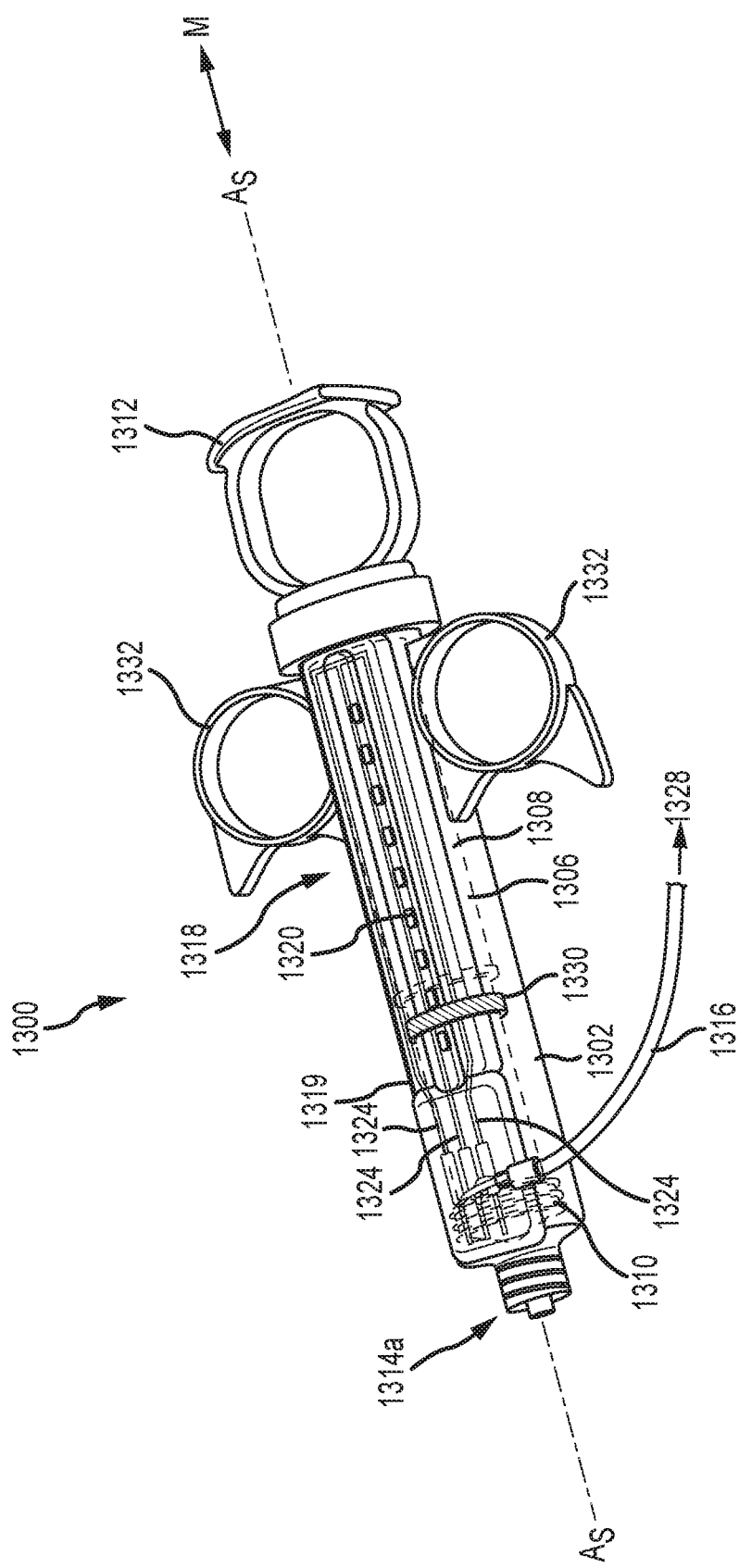
FIG. 13 depicts a perspective view of a second embodiment of a monitoring syringe utilizing a Hall sensor module.

FIG. 13 depicts a perspective view of a second embodiment of a monitoring syringe 1300 utilizing a Hall sensor module. The monitoring syringe 1300 includes a syringe housing 1302 defining a hollow inner bore. A plunger 1306 including a shaft 1308 and a piston 1310 is slidably received in the bore. More specifically, the piston 1310 may be slidably engaged with an interior surface of the bore and linear movement M of the shaft 1308, within the bore, moves the piston 1310. Movement M is along the syringe axis $A_S$. The plunger 1306 is moved back and forth within the bore 1304 by the movement of a thumb pad, such as a thumb-ring 1312. As the plunger 1306 is moved M in a direction towards the discharge end 1314a of the syringe housing 1302, the fluid contained therein is discharged into a manifold assembly, tube, or needle (not shown) and delivered to a patient.

As an alternative embodiment to that depicted in FIGS. 10-11, a Hall sensor module 1318 may be secured to an exterior surface of the syringe housing 1302, rather than securement to the plunger. The Hall sensor module 1318 includes a Hall sensor housing 1319 that encloses a plurality of Hall sensors 1320. As described above with regard to FIGS. 9-11, a greater number of discrete Hall sensor elements may improve accuracy. One or more leads or wires 1324 extend from an end of the Hall sensor module 1318. A cable 1316 connects at an end 1328 to an interface unit that analyzes the output of the Hall sensor module 1318 and provides this information to a user of the monitoring syringe 1300, typically on a display. In other embodiments, communication may be via a radio, Bluetooth, of other wireless connection, as described herein. The displayed information may include volume of the chamber, volume remaining, volume dispensed, fluid type, flow rate, fluid pressure or temperature and/or other information, as required or desired for a particular application. As described above, the signals from the Hall sensors may first be processed by an associated circuit board then sent to an interface unit, or the discrete signals may be sent to the interface unit for processing.

In the depicted embodiment, the shaft 1308 of the plunger 1306 has one or more magnets 1330 disposed thereon or within the shaft 1308. The magnet 1330, in this case, includes a plurality of arc magnets disposed about the shaft 1308. As the plunger 1306 is slidingly moved M along the axis $A_S$, the magnet 1330 passes in front of the Hall sensors 1320 of the Hall sensor module 1318. The magnetic field generated by the magnet 1330 is detected by the Hall sensor 1320. The Hall sensor 1320 sends a signal to the interface unit that determines the position of the plunger 1306 within the syringe housing 1302, based on the position of the magnet 1330 as detected by an individual Hall sensor 1320. Thus, the position of the plunger 1306 can be determined. The interface may also determine the various types of information listed above, based on a known diameter and length of the bore 1304 of the syringe housing 1302. Two finger rings or tabs 1332 receive the fingers of a user during use. A stop 1334 prevents the plunger 1306 from being pulled out of the syringe housing 1302.

Although the embodiments depicted in FIGS. 9-13 depict a plurality of Hall sensors, other embodiments of monitoring syringes may utilize one or more sensors of various types. For example, a single sensor, or multiple sensors, may be used to measure a magnetic field, material resistance, capacitance, etc. The measurements from such sensors may be utilized to determine the linear position of the plunger within the syringe. Examples of such sensors include, but not limited to, Hall effect sensors (as described in more detail herein), inductive sensors, capacitive touch sensors, and others.

Figure 7A:
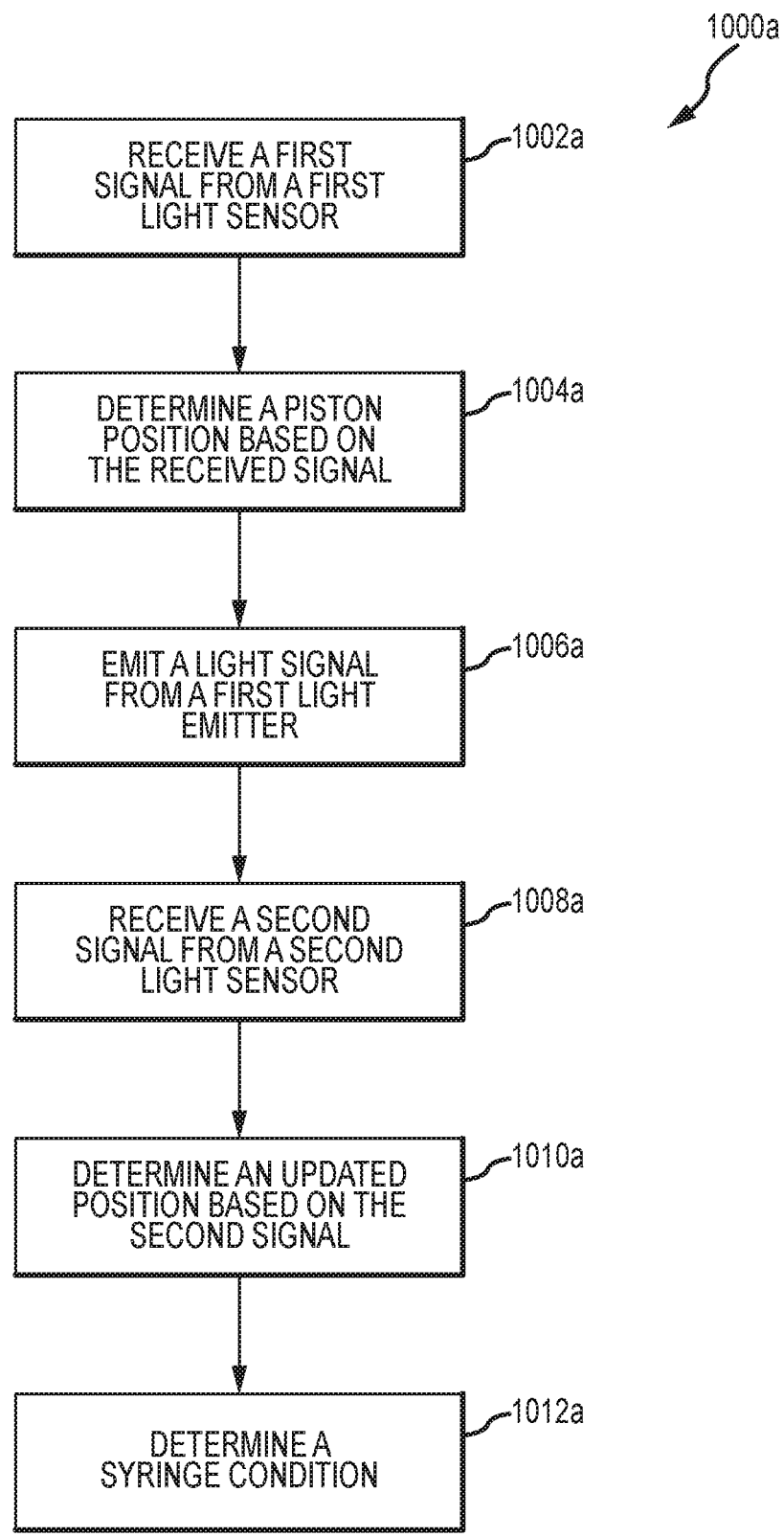
FIG. 7A depicts a first method of using a monitoring device.

FIG. 7A depicts a first method 1000a of using a monitoring syringe utilizing light signals. At operation 1002a, a signal is received from a light sensor, the position of which on a monitoring syringe is known. Other characteristics of the light sensor, such as receptive wavelength, may be known. Based on the position of the light sensor and the signal received from said sensor, a position of a piston is then determined in operation 1004a. In certain embodiments of the method 1000a, a light signal is emitted from the first emitter in operation 1006a. In embodiments where multiple light sensors are used, a light signal may be received at a second light sensor having known characteristics (e.g., position) in operation 1008a. An updated position may then be determined based on the characteristic of the second light sensor and the signal in operation 1010a. At any time a light signal is received from a known light sensor, a condition of the syringe (such as those described herein) may be determined, as in operation 1012a.

Figure 7B:
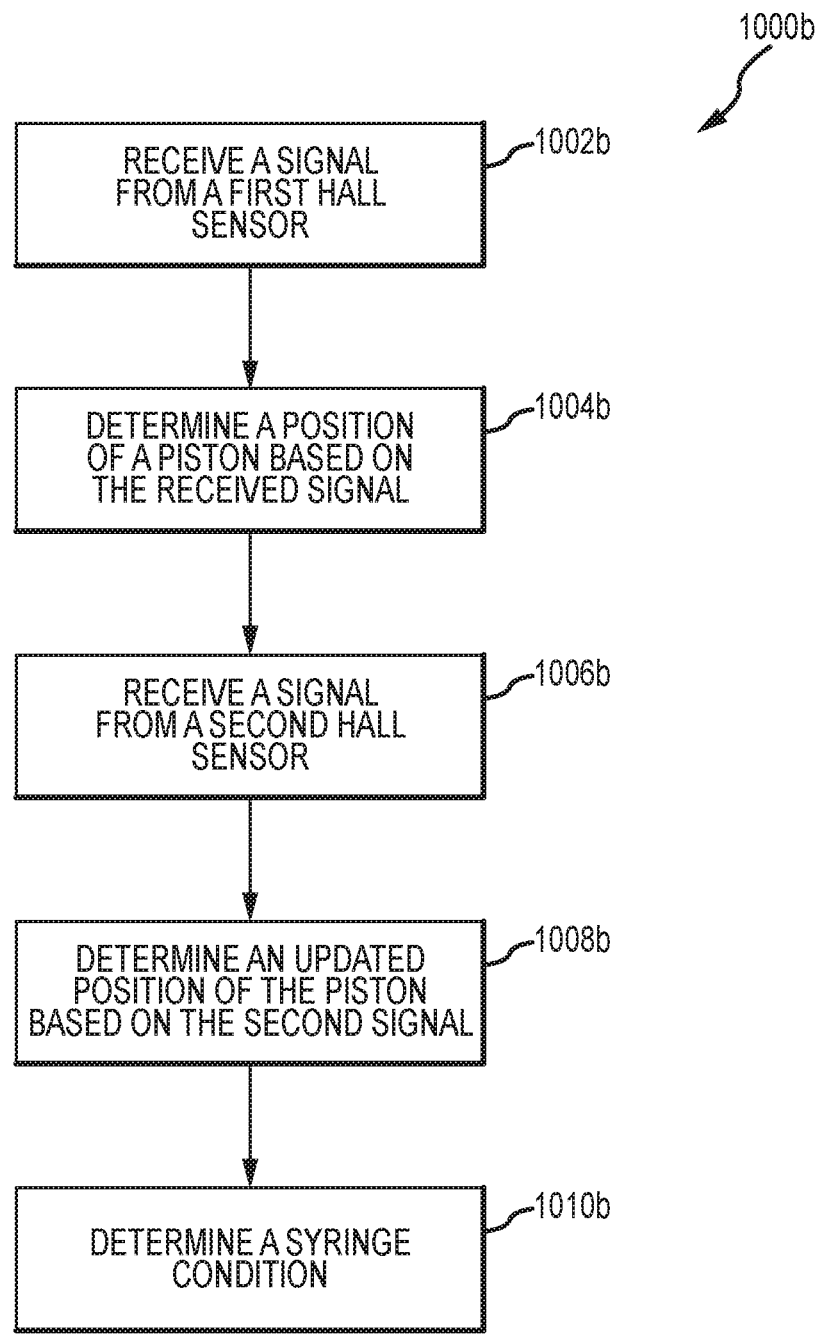
FIG. 7B depicts a second method of using a monitoring device.

FIG. 7B depicts a second method 1000b of using a monitoring syringe utilizing Hall sensors. At operation 1002b, a signal is received from a first Hall sensor, the position of which in a plunger shaft is known, relative to other Hall sensors in the shaft. Based on the position of the first Hall sensor and the signal received from said sensor, a position of a piston is then determined in operation 1004b. Since a cross-sectional area, diameter, or other dimension of the syringe is known, the amount of media in the syringe based on the position of the piston can be determined. In embodiments where multiple Hall sensors are used, a signal may be received from a second Hall light sensor having known characteristics (e.g., position) in operation 1006b. An updated position of the piston may then be determined based on the received signal from the second Hall sensor and the signal in operation 1008b. At any time a signal is received from a known Hall sensor, a condition of the syringe (such as those described herein) may be determined, as in operation 1010b. As described above, the method 1000b may be performed on the circuit board within the monitoring syringe, then sent to an associated system via the transmitter for further analysis or display to a surgeon, etc. In an alternative embodiment, each signal may be sent via the transmitter to an associated system for processing, analysis, display, etc.

In addition, the methods described in FIGS. 7A-7B, when used in a system employing a diversion reservoir, may further incorporate a measurement determined in a chamber collecting medium diverted from an injection (i.e., through a modulator). Having a total amount of medium injected by the syringe (as determined by a sensing apparatus), minus the amount of medium diverted (as determined by a sensing apparatus), provides the total amount of the injection actually delivered to the patient.

Figure 8:
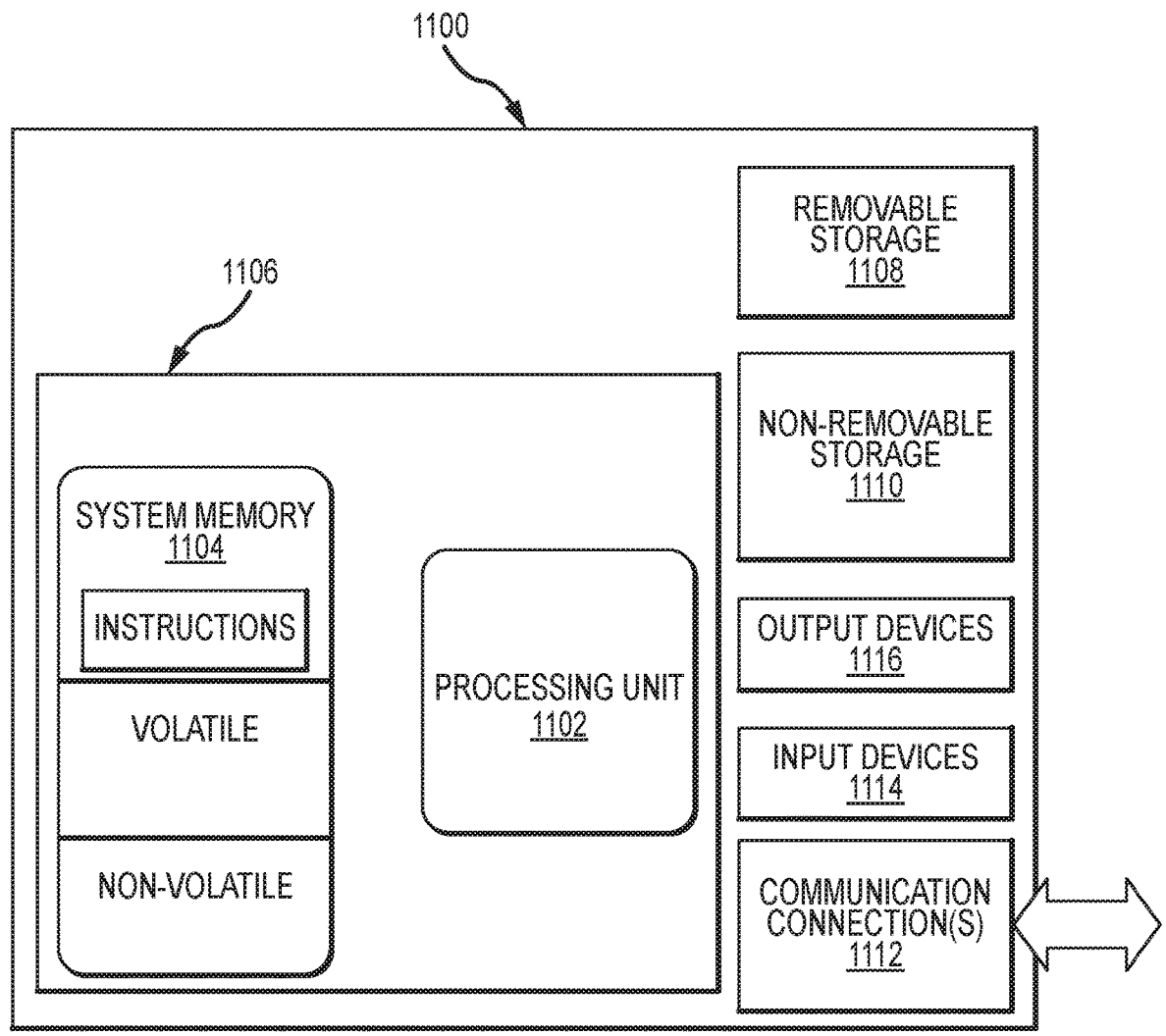
FIG. 8 depicts one example of a suitable operating environment in which one or more of the present examples may be implemented.

FIG. 8 illustrates one example of a suitable operating environment 1100 in which one or more of the present embodiments may be implemented. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 1100 typically includes at least one processing unit 1102 and memory 1104. Depending on the exact configuration and type of computing device, memory 1104 (storing, among other things, instructions to perform the monitoring methods described herein) may be volatile (such as RAM), nonvolatile (such as ROM, flash memory, etc.), or some combination of the two. This most basic configuration is illustrated in FIG. 8 by line 1106. Further, environment 1100 may also include storage devices (removable, 1108, and/or non-removable, 1110) including, but not limited to, magnetic or optical disks or tape. Similarly, environment 1100 may also have input device(s) 1114 such as touch screens, keyboard, mouse, pen, voice input, etc. and/or output device(s) 1116 such as a display, speakers, printer, etc. Also included in the environment may be one or more communication connections, 1112, such as LAN, WAN, point to point, Bluetooth, RF, etc.

Operating environment 1100 typically includes at least some form of computer readable media. Computer readable media can be any available media that can be accessed by processing unit 1102 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1100 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet. In some embodiments, the components described herein comprise such modules or instructions executable by computer system 1100 that may be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 1100 is part of a network that stores data in remote storage media for use by the computer system 1100.

The monitoring syringes such as those described above may be utilized in various types of medium management systems to control and monitor medium injection into patients. Two exemplary medium management systems, as well as components thereof, are described below in the following figures. These are but two types of systems that may benefit from the monitoring technologies described herein. Other systems and configurations thereof will be apparent to a person of skill in the art.

Figure 14:
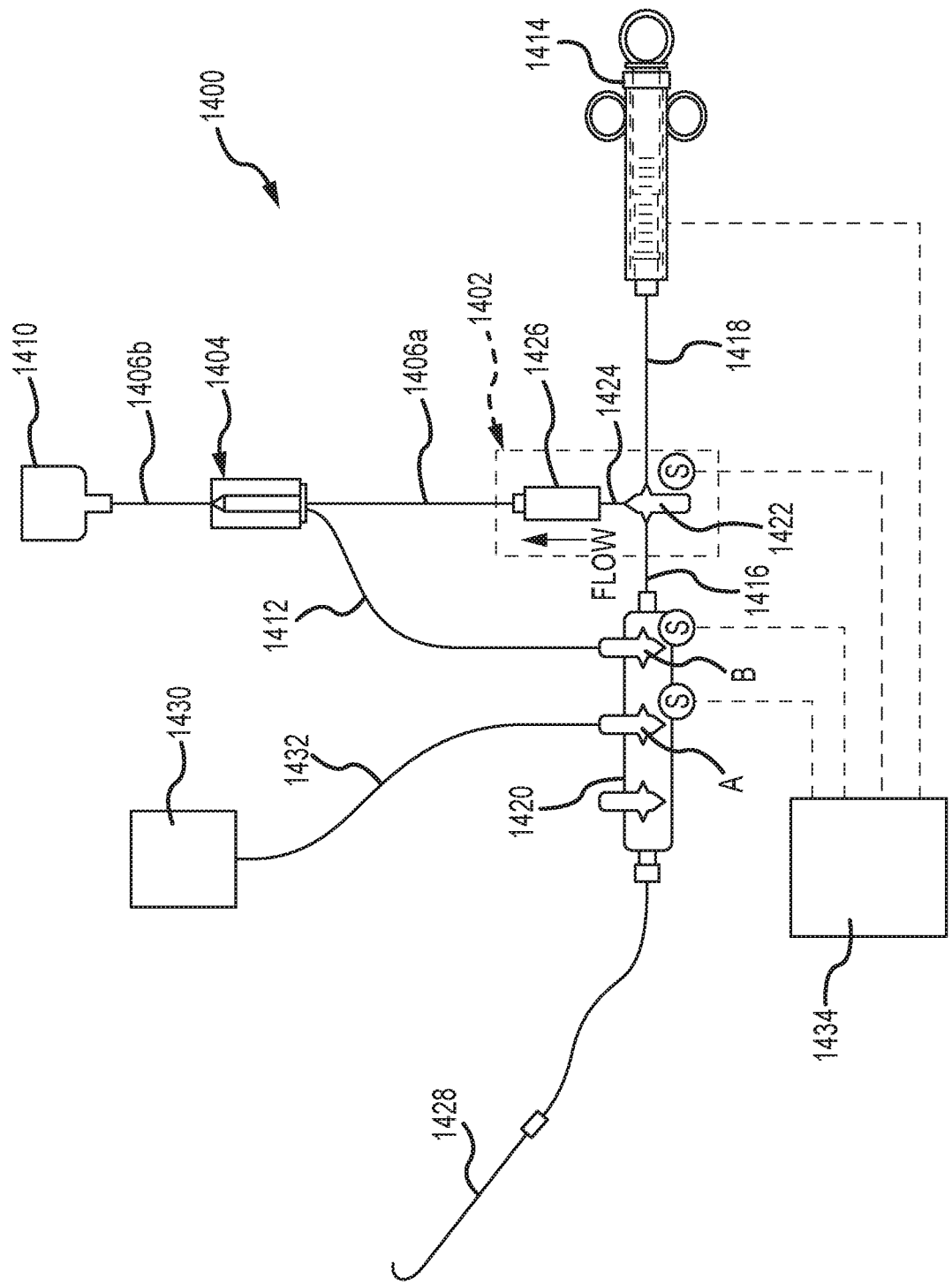
FIG. 14 illustrates an exemplary medium management system.
Figure 15C:
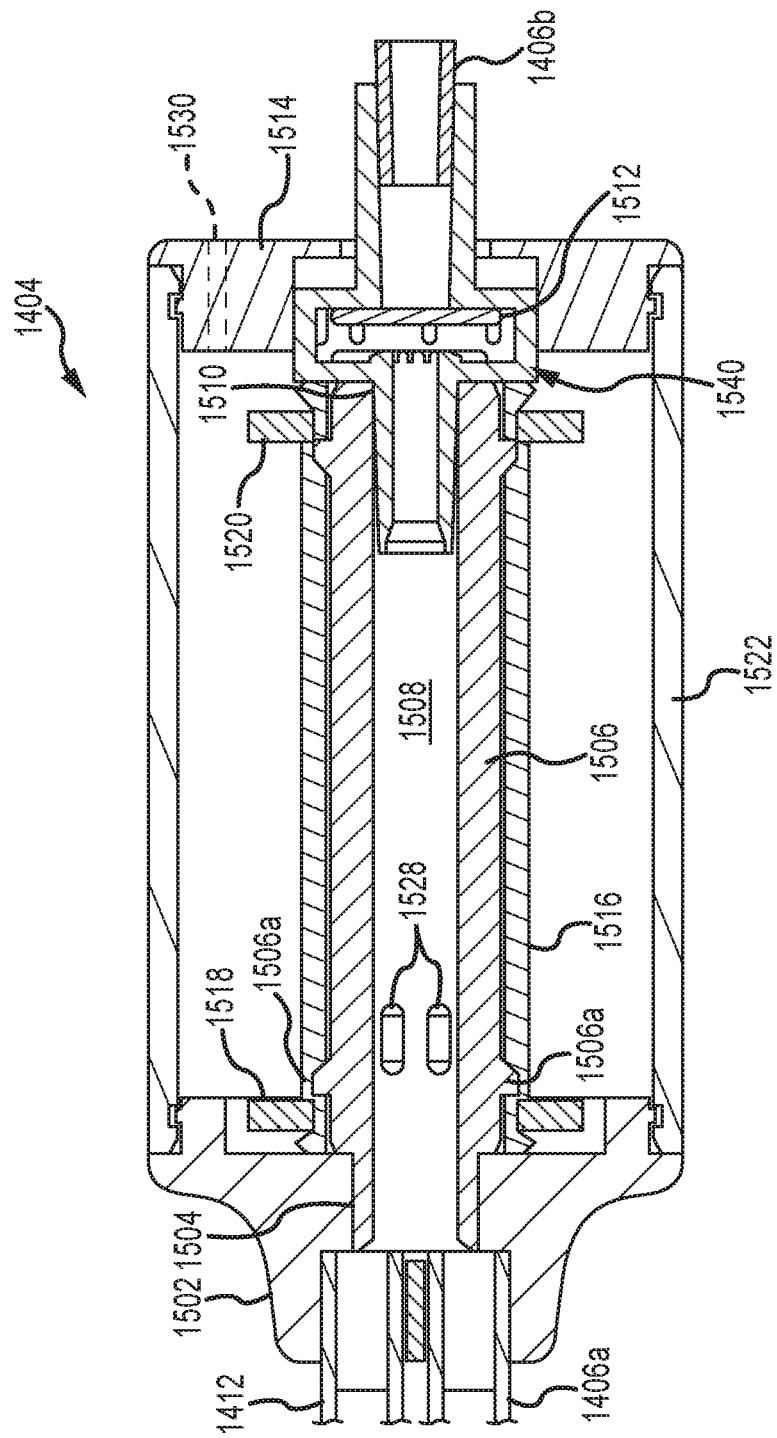
FIG. 15C is a cross-sectional view of the exemplary medium diversion reservoir in a first configuration, taken along line 15C-15C of FIG. 15A.
Figure 15D:
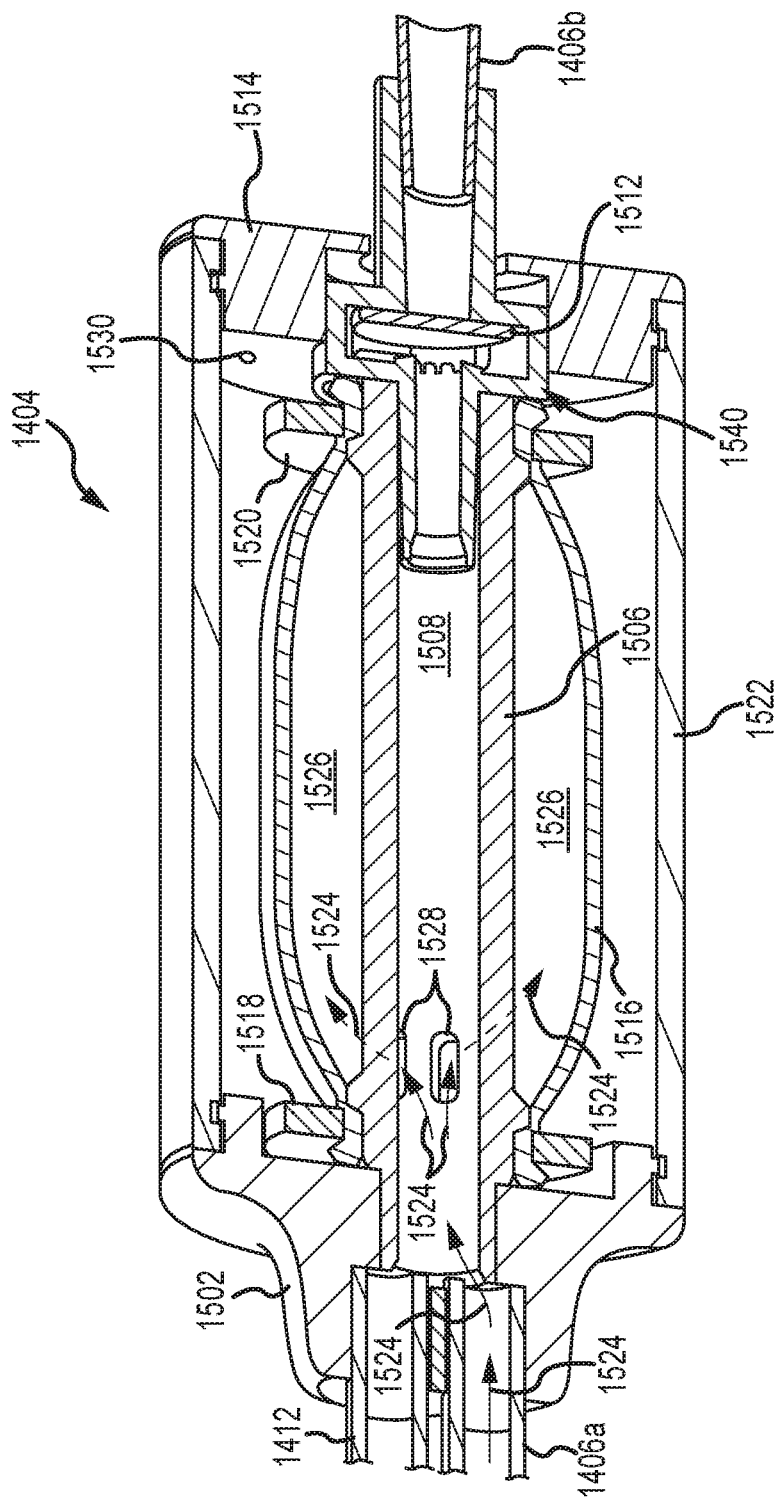
FIG. 15D is a cross-sectional view of the exemplary medium diversion reservoir in a second configuration, taken along line 15C-15C of FIG. 15A.
Figure 16:
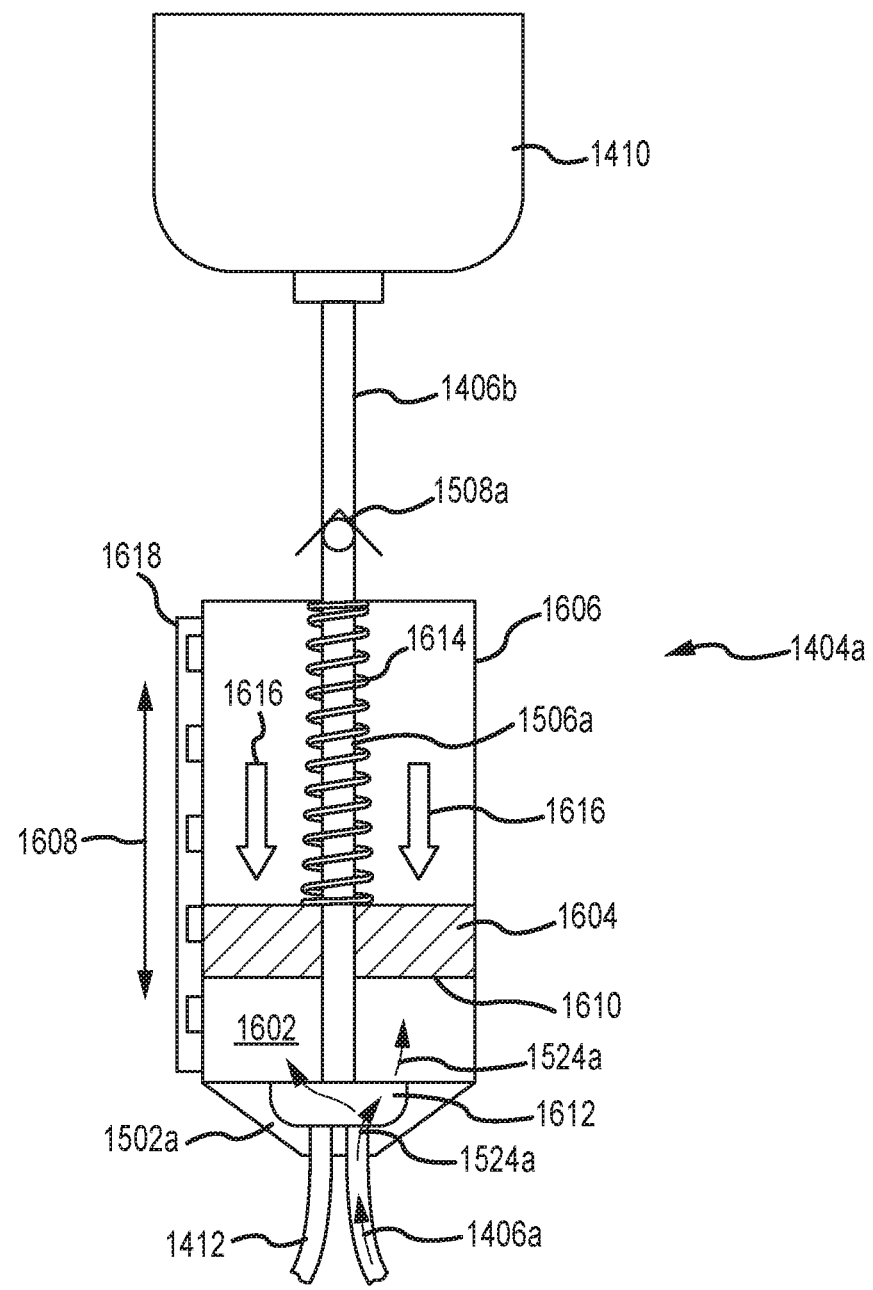
FIG. 16 illustrates another exemplary medium diversion reservoir.

FIGS. 14-16 illustrate another medium management system 1400 that may include, as shown in the illustrated embodiment, a flow diverter assembly (i.e., a modulator) 1402 and a diversion reservoir 1404. In this embodiment, tubular member 1406a extends from the valve 1426 of the flow diverter assembly 1402 to a medium diversion reservoir 1404, and tubular member 1406b extends from diversion reservoir 1404 to medium reservoir (e.g., contrast agent vial) 1410. Medium from the medium reservoir 1410 (e.g., contrast agent vial) is permitted to flow away from the medium reservoir 1410 and through diversion reservoir 1404 via tubular members 1406b and tubular member 1412. In the illustrated arrangement (of FIG. 14), syringe 1414 may be fluidly coupled to medium reservoir 1410 by tubular members 1406b, 1412, 1416 and 1418, coupling those components together by a manifold 1420 and through stopcock 1422. When the syringe 1414 is being loaded with medium from medium reservoir 1410, the stopcock 1422 may be positioned to permit medium flow between tubular members 1416 and 1418, but not to tubular member 1424 disposed between the stopcock 1422 and the valve 1426 of the flow diverter assembly 1402. The syringe 1414 may be any of the monitoring syringes described herein (e.g., using light sensors, Hall sensors, etc.) or of the monitoring syringes known in the art. Drawing back the syringe 1414 may pull medium from the medium reservoir 1410 through tubular member 1406b, and/or diversion reservoir 1404, and through tubular member 1412. Medium from the medium reservoir 1410 and/or medium residing in the diversion reservoir 1404 may then be further drawn, into and toward, syringe 1414 through tubular members 1416 and 1418. Once the syringe 1414 is loaded with medium from medium reservoir 1410 and/or diversion reservoir 1404, valve B on manifold 1420 may then be manipulated to prohibit flow back to medium reservoir 1410 and diversion reservoir 1404 via tubular member 1412 (and such flow may be further inhibited by a check valve disposed between diversion reservoir 1404 and medium reservoir 1410), and the stopcock 1422 may be positioned to allow flow through the tubular members 1418, 1424, 1416 and manifold 1420.

During contrast injection procedures incorporating a modulator (such as flow diverter assembly 1402) a portion of the injected medium flow from the syringe 1414 may be diverted away from the medium flow path to injection catheter 1428 by the flow diverter assembly 1402. In the modulation/reservoir system 1400 illustrated in FIGS. 14-16, such diverted medium flow passing through the flow diverter assembly 1402 flows into the diversion reservoir 1404, as opposed to the diverted medium flowing directly into the medium reservoir 1410 or some other outflow/overflow reservoir/chamber. Advantageously, the diversion reservoir 1404 provides means for collecting overflow medium diverted by the flow diverter assembly 1402, for possible re-use as the syringe 1414 may be again activated to pull medium into the system (e.g., for introduction into the patient via catheter 1428). The use of such a diversion reservoir in this manner, with an associated check valve preventing back flow of medium into the medium reservoir 1410, allows for capture and re-use of medium that is already introduced into the system (e.g., in the diversion reservoir 1404) while preserving the integrity of the medium disposed within medium reservoir 1410 in its original form.

The medium management system 1400 may also include a saline reservoir 1430 that can be used to flush portions thereof. In the depicted system 1400 of FIG. 14, the saline reservoir 1430 is connected to the manifold 1420 via a tube 1432 and can be isolated from the remainder of the system 1400 with valve A. Valve A may include a position or other sensor S that detects a position of the valve A. A flush signal is sent from the valve A sensor S to a monitoring/display system 1434, which also may be configured to monitor the positon of valve B and stopcock 1422 (using sensors S), as well as the output from the various sensors on the monitoring syringe 1414 and/or the sensors on the diversion reservoir 1404. For example, when the valve A is in an open position, the monitoring/display system 1434 may disregard signals from the monitoring syringe 1414 and/or diversion reservoir 1404 (as those readings are not reflective of contrast being injected from or drawn into the syringe 1414). In another example, if the valve A is in an open position, the monitoring/display system 1434 may display an instruction or emit a signal to remind an operator to close valve B and/or stopcock 1422 so as to isolate those portions of the system 1400. In another, more complex example, the system 1400 uses automated valve B and/or stopcock 1422 and closes these valves upon receiving an open signal from valve A.

One embodiment of the diversion reservoir 1404 is illustrated in FIGS. 15A-15D. FIG. 15A shows an assembled view of diversion reservoir 1404 along with its associated tubular members 1406a and 1412. FIG. 15B is an exploded view of the assembly of FIG. 15A. The system 1400 may further include a second supply conduit 1412 in fluid communication with the supply conduit 1406b and the diversion conduit 1406a, wherein the second supply conduit 1412 is fluidly coupled to the fluid medium flow path. Tubular members 1406a and 1412 are sealably connected to a first end cap or manifold 1502 on diversion reservoir 1404, as further shown in FIG. 15C, which is a sectional view taken through lines 15C-15C in FIG. 15A. A first end of a through-tube 1506 is sealably connected to an interior side of first end cap 1502, as at 1504. Through-tube 1506 includes an inner conduit 1508 extending therethrough. Inner conduit 1508 is in fluid communication with the interiors of tubular members 1406a and 1412 via their adjacent couplings in the first end cap 1502, as illustrated in FIG. 15C. A second end of through-tube 1506 is sealably connected to a check valve assembly 1540, as at 1510, and the inner conduit 1508 is in fluid communication with the check valve assembly 1540. The check valve assembly 1540 is, in turn, in fluid communication with the tubular member 1406a. As seen in FIG. 15C, the check valve assembly 1540 includes a moveable valve plate 1512 (or other suitable structure allowing one way flow through the valve) which is operable to permit flow from the medium reservoir 1410 (e.g., medium contrast vial) via tubular conduit 1406b into the inner conduit 1508 of through-tube 1506, but to inhibit flow in reverse thereof. This arrangement may allow flow of medium from fluid reservoir 1410 via tubular conduit 1406b, inner conduit 1508 of through-tube 1506, and tubular conduit 1412 to the syringe 1414. Moreover, medium flow diverted by flow diverter assembly 1402 may also be permitted to flow via tubular member 1406a into inner conduit 1508 of through-tube 1506, but inhibited from flowing to the medium reservoir 1410 by check valve assembly 1540. A second end cap 1514 on diversion reservoir 1404 is secured about the check valve assembly 1540.

The diversion reservoir 1404 is designed to accommodate flow of medium from the flow diverter assembly 1402, to collect and hold such medium and then, if desired, urge such collected medium back into the system for use in delivering additional medium to the patient via injection catheter 1428. In one embodiment to accomplish this end, diversion reservoir 1404 may include an elastic expansion tube 1516 disposed about through-tube 1506. As seen in FIGS. 15C and 15D, expansion tube 1516 extends along a portion of a length of through-tube 1506. Expansion tube 1516 may be formed of silicone (or like flexible) material sealably secured adjacent each end thereof about the through-tube 1506 by first and second retention washers 1518 and 1520, respectively, or by other suitable sealable and mechanical fastening arrangements. An outer surface of the through-tube 1506 may include interference elements such as surface features or an annular interference rim 1506a (see FIG. 15C) to further facilitate the sealing of the expansion tube 1516 to the through-tube 1506 via the retention washer 1518 and 1520.

A housing tubular outer shell 1522 may be connected between the first end cap 1502 and second end cap 1514, thereby covering the expansion tube 1516 and other diversion reservoir components therein. The shell 1522 may serve to protect the components of the diversion reservoir 1404 therein, limit the extent of inflation or expansion of expansion tube 1516, and/or (if the shell 1522 is either transparent or translucent) allow observation of the condition (e.g., expanded state) of expansion tube 1516 therein.

FIG. 15D illustrates the diversion reservoir 1404 in perspective sectional view (again, as taken along lines 15C-15C in FIG. 15A) with the expansion tube 1516 shown in an exemplary stretched and expanded state, as opposed to its relaxed state shown in FIG. 15C. The expansion tube 1516 of the diversion reservoir 1404 receives medium flow from the flow diverter assembly 1402, via tubular member 1406a. This medium flow, as illustrated by flow arrows 1524 in FIG. 15D, flows from tubular member 1406a into the inner conduit 1508 of through-tube 1506 adjacent the first end of through-tube 1506. Through-tube 1506 can be a portion of the medium supply conduit 1406b that resides within reservoir chamber 1526. Flow out of the through-tube 1506 is inhibited at its second end by the check valve assembly 1540. However, the supply conduit through-tube 1506 may have one or more apertures 1528 therethrough which allows an interior of the expansion tube 1516 to be in fluid communication with the inner conduit 1508 and reservoir chamber 1526. Medium from the flow diverter assembly 1402 can thus flow through apertures 1528 and into a medium reservoir or chamber 1526 defined by the expansion tube 1516. This medium chamber 1526 is defined between the inner surface of expansion tube 1516 and the outer surface of through-tube 1506, whereby the expansion tube 1516 forms an elastic bladder disposed around the supply conduit 1506, with the walls of expansion tube 1516 capable of imparting a force on the fluid medium within the chamber 1526. A surface within chamber 1526 is capable of imparting a variable or constant force on the fluid medium within the chamber 1526, and the surface is defined at least in part by a wall of the elastic bladder of expansion tube 1516. The medium chamber 1526 thus receives and collects the diverted portion of the flow of medium from the flow diverter assembly 1402. The diversion reservoir 1404 comprises a variable or constant force biasing member disposed relative to at least one surface within the reservoir chamber 1526 to urge the surface against the fluid medium within the reservoir chamber 1526. The expandable wall of the expansion tube 1516 thus defines a surface within the medium chamber 1526 capable of imparting a force (variable or constant) on the fluid medium within the medium chamber 1526. In one embodiment, the second end cap 1514 includes an aperture 1530 therethrough to permit the escape of gas within the cover 1522 and thereby readily permit expansion of the expansion tube 1516 therein.

In use, as the pressure of medium within the flow diverter assembly 1402 increases enough to allow flow therethrough, medium flows from the diverter valve 1426 via the tubular member 1406a to the diversion reservoir 1404. Fluid coupling is provided by a medium supply conduit 1406b disposed between, and fluidly coupled to, the diversion reservoir 1404 and the sterile medium container 1410. A diversion supply conduit 1406a is disposed between, and fluidly coupled to, the diversion reservoir 1404 and the flow diverter assembly 1402 so as to supply the reservoir 1404 with the diverted portion of the fluid medium from the flow diverter assembly 1402. Medium flows within the diversion reservoir 1404 as illustrated by arrows 1524 into medium chamber 1526, thereby stretching the walls of the expansion tube 1516 and expanding chamber 1526 to accommodate the diverted medium flow. Accordingly, as the medium pressure provided via syringe 1414 increases in the system, the flow diverter assembly 1402 relatively diverts medium so that the flow to the patient relatively increases as relatively less flow is diverted by the flow diverter assembly 1402 into the diversion reservoir 1404. The medium contained in the chamber 1526 may be available for further infusion into the patient via the modulation/reservoir system 1400. As an example, an operator may activate valve B to allow medium flow from the chamber 1526 of the diversion reservoir 1404 into the syringe 1414 (which is being withdrawn to draw such fluid therein). If the fluid needed is greater than the volume retained within the chamber 1526, the force of check valve 1512 is overcome and further medium is withdrawn from the medium reservoir 1410 (e.g., contrast agent vial). Once a sufficient amount of medium has been withdrawn from the chamber 1526 and/or reservoir chamber 1410, valve B may be closed and the modulation/reservoir system 1400 may be again in condition for delivery of medium via injection catheter 1428, by activation of injection syringe 1414 by an operator. As long as the stopcock 1422 is disposed to allow flow into tubular members 1416 and 1424, the flow modulator assembly 1402 may automatically activate to divert excess medium, thereby ultimately reducing the amount of medium introduced into the patient via injection catheter 1428 (e.g., thus introducing no more medium than necessary to attain operative opacity). In one embodiment shown, as the pressure is increased in the modulator 1402, the resistance to medium flow into the diversion circuit is increased by operation of the flow diverter assembly 1402. The process may be repeated by an operator as many times as deemed necessary to complete the procedure desired. Use of the modulation/reservoir system 1400 in this manner may achieve the advantageous reduction of introduction of unnecessary medium into the patient while achieving the necessary amount and flow of medium in the patient for diagnostic or treatment means (e.g., for opacity). In addition, the diversion reservoir 1404 may allow re-use of the diverted outflow of medium.

The diversion reservoir illustrated in FIGS. 15A-15D presents one form of such a reservoir. Alternative forms are contemplated as well. For example, an alternative form of elastic bladder or elastic surface may be provided that functionally allows the receipt of medium overflow from the flow diverter assembly 1402 into an expansion chamber, and then further allows the flow of medium from the medium reservoir 1410 through the diversion reservoir 1404 and into the modulation/reservoir system 1400 for use. An alternative means of placing force on the medium within the chamber in the diversion reservoir 1404 may be attained by a bias plunger, such as illustrated schematically in FIG. 16. The diverted portion of the fluid medium flows through a diversion conduit 1406a away from the flow diverter assembly 1402. The system 1400 comprises a medium reservoir 1410 containing a supply source of fluid medium for the system 1400 and a supply conduit 1406b through the reservoir chamber 1602 that fluidly connects the medium reservoir 1410 and the diverter conduit 1406a. The supply conduit 1406b comprises a check valve 1508a to prevent the flow of fluid medium from the supply conduit 1406b into the medium reservoir 1410. Diversion reservoir 1404a includes a plunger 1604 slidably disposed in housing 1606 and moveable in a linear fashion relative to the housing 1606, as illustrated by movement line 1608. Thus, the surface 1610 is movable in a linear direction relative to the fluid medium within the reservoir chamber 1602. A proximal face or surface 1610 of the plunger 1604 thus defines a portion of a chamber 1602 within the housing 1606 for diverted medium that is received therein via the tubular member 1406a.

Like the diversion reservoir 1400 illustrated in FIGS. 15A-15D, diversion reservoir 1404a may include a first end cap 1502a that acts as a manifold for medium flow. Tubular member 1406a is connected to first end cap 1502a, as is tubular member 1412. Chamber 1602 is in fluid communication with the interiors of tubular members 1406a and 1412, such as via manifold 1612 within the first end cap 1502a, as seen in FIG. 16. A through-tube 1506a is also in fluid communication with the manifold 1612, and extends through the housing 1606 of the diversion reservoir 1404a to a check valve 1508a. Check valve 1508a permits medium flow from medium reservoir 1410 via tubular member 1406b into through-tube 1506a but prevents backflow. Medium from the medium reservoir 1410 can then flow from the diversion reservoir 1404a into the syringe 1414 via tubular member 1412.

When medium is diverted by the flow diverter assembly 1402 into the diversion reservoir 1404a, medium flows as illustrated by flow arrows 1524a from tubular member 1406a, through manifold 1612, and into the chamber 1602. The diversion reservoir 1404a comprises a variable or constant force biasing member such as spring 1614 disposed relative to at least one surface 1610 within the reservoir chamber 1602 to urge the surface 1610 against the fluid medium within the reservoir chamber 1602. In an exemplary embodiment, surface 1610 is planar. The face 1610 of the plunger 1604 is biased by spring 1614 toward the manifold chamber 1612, and thus defines a moveable surface 1610 for the chamber 1602 that can move away and expand chamber 1602 as more medium is introduced therein, when the bias of the force acting against it is overcome. This bias acts on the plunger 1604 within the housing 1606, as illustrated schematically by force arrows 1616, and such force may be achieved by suitable means such as springs, weight distribution, linear actuator, or other force elements. The use of a linearly moving plunger 1604 (as its movement is illustrated by arrows 1608) may permit more ready measurement of how much medium has actually been diverted by the flow diverter assembly 1402 and thereby, by derivation, how much medium has actually been delivered to a patient by the injection catheter 1428. Measurement may be performed by utilizing a light-based, Hall sensor-based, or other type of monitoring system 1618 disposed in or on the housing 1606, or in or on other structures (such as the plunger) of the diversion reservoir 1404, as such systems are described herein. The plunger 1604 thus provides a linear expansion element (surface 1610) that serves to apply force to the overflow medium collected for possible re-use in the chamber 1602.

Figure 17:
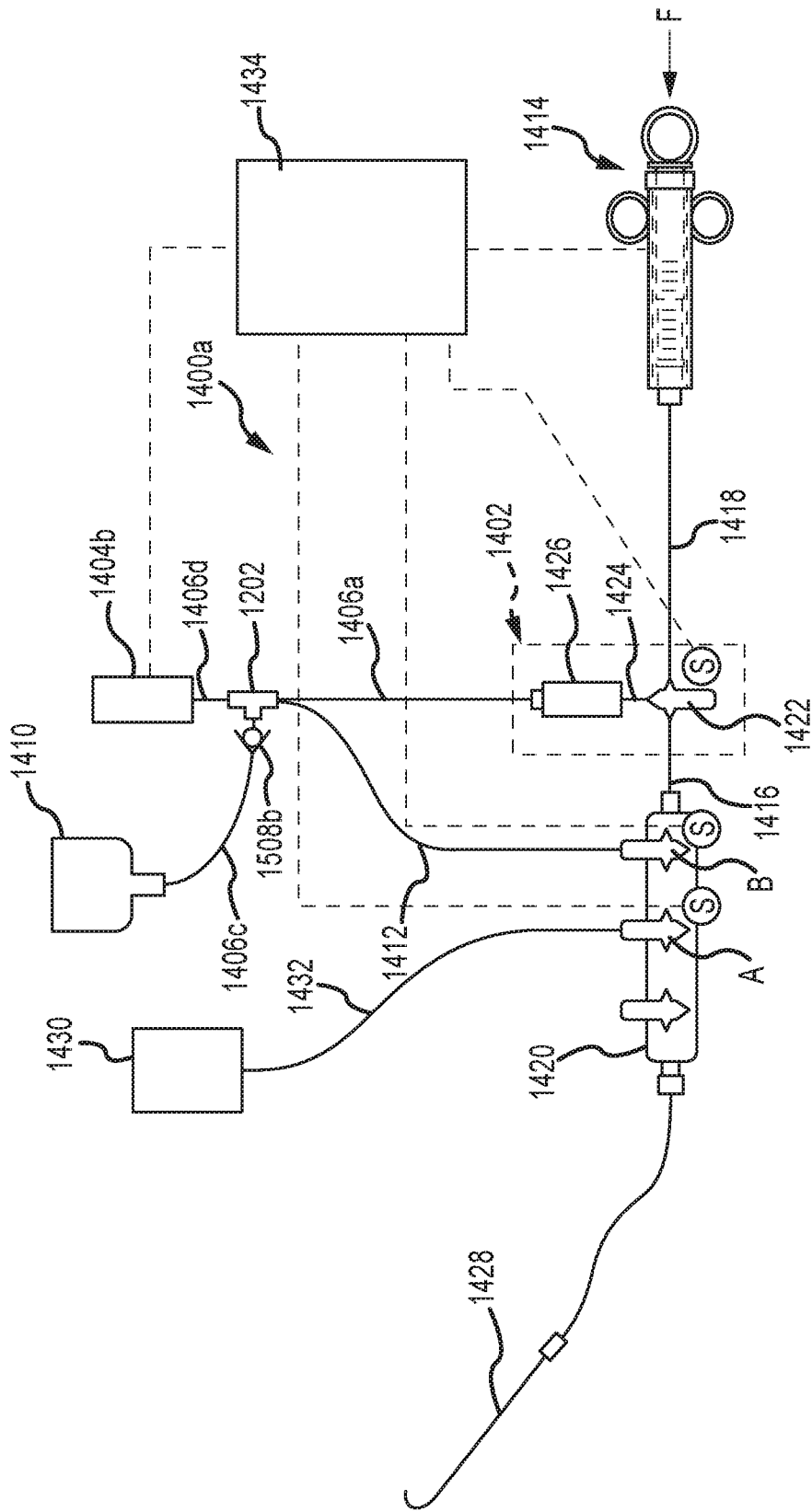
FIG. 17 illustrates another exemplary medium management system.

The diversion reservoir 1404a operates in a similar manner to the diversion reservoir 1404, discussed above, by providing an expandable chamber for medium diverted by the flow diverter/modulating assembly 1402, wherein the chamber (e.g., chamber 1602, 1526) has at least one surface acting upon it to urge the medium therein back toward the injection device 1414 (via conduit 1412) for possible re-use. Likewise, medium which has been diverted by the flow diverter assembly 1402 into the diversion reservoir chamber 1602 is not permitted to flow back to the diverter assembly 1402, nor to flow to the medium reservoir 1410 (via check valve 1508a). In alternative embodiments for modulation/reservoir systems, the diversion reservoir is configured so that flow through it to the medium reservoir 1410 is not permitted or necessary. One such arrangement is illustrated in FIG. 17, in connection with a modulation/reservoir system 1400a. In these arrangements, there may be no necessity for a through-tube arrangement through the diversion reservoir. The diversion reservoir simply provides an expandable chamber therein for retaining and re-using medium diverted from the flow diverter assembly 1402. Such diversion reservoirs 1404b may employ a bladder form of chamber or a constant or variable force resistance form of chamber, such as those illustrated and discussed herein, where at least one surface therein is capable of imparting a sufficient force upon the fluid medium within the chamber. For example, the diversion reservoir 1404b may be constructed to function similar to the spring-based monitoring syringe 1200 depicted in FIG. 11. Although the "injection function" of the syringe 1200 may not be needed to function as a diversion reservoir, one can see the advantages of using the measurement capabilities derived from the chamber as described in FIG. 11 as it might function as a "diversion reservoir", utilizing spring 1209 to bias piston 1210. FIG. 17 illustrates an arrangement where the medium reservoir chamber 1410 is connected via tubular member 1406c to a T-connector 1702 disposed between a diversion reservoir 1404b (without a through-tube) and the flow diverter assembly 1402. The T-connector 1702 connects at its first end to the tubular members 1412 and 1406a and at its second end to tubular member 1406d that leads to the diversion reservoir 1404b. A side fitting of the T-connector 1702 leads via tubular member 1406c to the medium reservoir 1410. A check valve 1508b is disposed between the T-connector 1702 and the medium chamber 1410 to prevent back flow of medium from the flow diverter assembly 1402 and/or diversion reservoir 1404b into the medium container 1410. In operation, the configuration illustrated in FIG. 17 may be similar to that described above with respect to FIG. 14. As the pressure of medium within the flow diverter assembly 1402 increases enough to allow flow therethrough, medium flows from the valve 1426 via tubular member 1406a to the T-connector 1702. Medium may then flow from the T-connector 1702 via tubular member 1406d to the diversion reservoir 1404b. Medium flowing into the diversion reservoir 1404b moves the piston therein to accommodate the diverted medium flow. In operation, medium provided via syringe 1414 may be diverted by the flow diverter assembly 1402 away from injection to the patient, and accumulate in the diversion reservoir 1404b.

The medium contained in the expandable chamber within the diversion reservoir 1404b may be available for further infusion into the patient via the modulation/reservoir system 1400a. To do so, an operator activates valve B to allow medium flow from the chamber within the diversion reservoir 1404b into the syringe 1414 (which is being withdrawn to draw such fluid therein). If the fluid needed is greater than the volume retained in the chamber reservoir 1404b, the force of check valve 1508b is overcome and further medium is then withdrawn from the medium reservoir 1410. Once a sufficient amount of medium has been withdrawn from the chamber within the diversion reservoir 1404b and/or reservoir chamber 1410, valve B is again closed and the modulation system 1400a is again in condition for delivery of medium via injection catheter 1428, by activation of injection syringe 1414 by an operator. As long as the stopcock 1422 is disposed to allow flow into tubular members 1416 and 1424, the flow diverter assembly 1402 will then again be automatically activated to divert excess medium when a threshold pressure for activation of the flow diverter assembly 1402 is attained, thereby ultimately reducing the amount of medium introduced into the patient via injection catheter 1428. Again, as pressure is increasing going into flow diverter system 1402, the flow through the diverter 1402 is relatively decreasing (thus, flow to the patient may be relatively increasing at the same time by operation of the flow diverter assembly 1402). The process can be repeated by an operator as many times as deemed necessary to complete the procedure desired. Use of the modulation/reservoir system 1400a in this manner achieves the advantageous reduction of introduction of unnecessary medium into the patient while achieving the necessary amount and flow of medium in the patient for the desired diagnostic or treatment process. Furthermore, the modulating/reservoir assembly may advantageously allow an operator to change out the injection delivery system (i.e., guide catheter, diagnostic catheter, treatment tools, etc.) without changing the flow modulator. Moreover, the diversion reservoir may allow simplistic re-use of the diverted medium.

Figure 18:
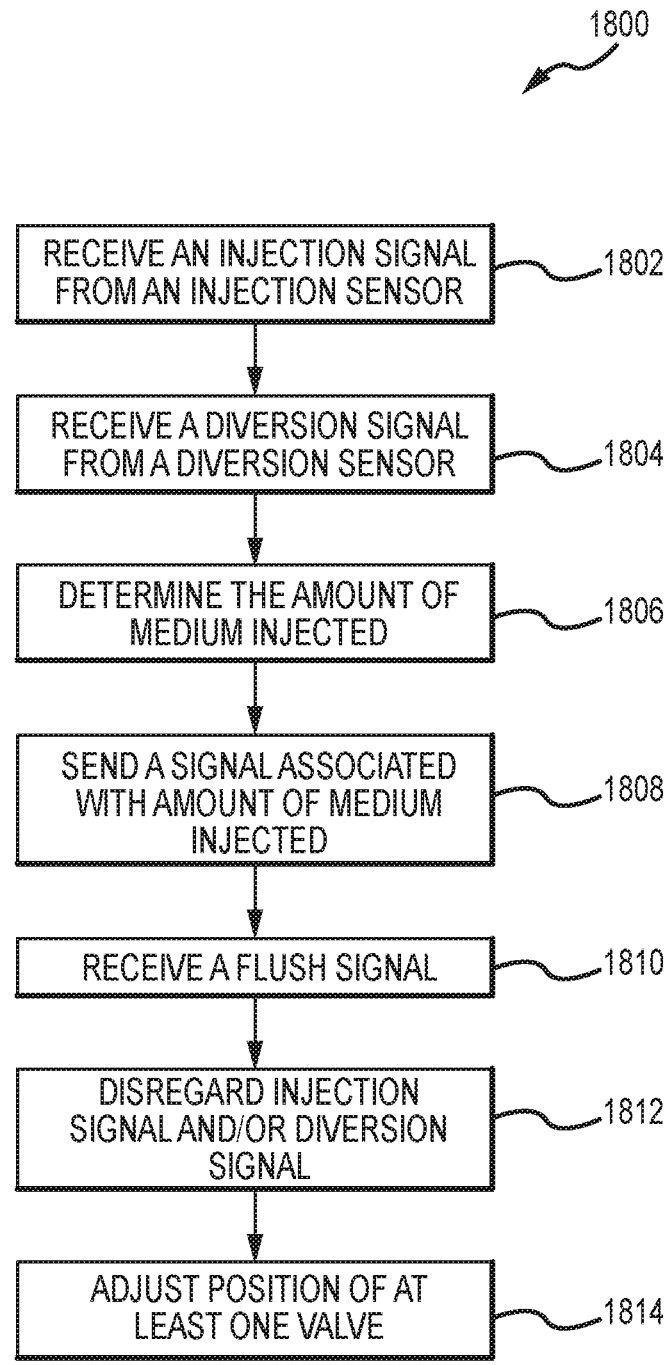
FIG. 18 depicts a method of determining an amount of medium injected into a patient.

FIG. 18 depicts a method 1800 of determining an amount of medium injected into a patient. The method begins at operation 1802, where an injection signal is received from a sensor associated with an injection syringe. In operation 1804, a diversion signal is received from a sensor associated with a diversion reservoir. Each of the injection signals and the diversion signals may be received from the various types of monitoring systems as described herein, including light-based sensor systems, Hall sensor-based systems, and so on. These signals can include position signals (e.g., position of the piston), which may be used to determine a volume of medium contained within the injection syringe and/or the diversion reservoir. With this information, the amount of medium injected may be determines based at least in part on the injection signal and the diversion signal, in operation 1806. In an example, the amount injected is the difference between the volume in the injection syringe minus the volume in the diversion reservoir. Operations 1802-1806 are constantly updated as medium is injected into the patient.

In operation 1808, a signal associated with the amount of medium injected is sent. The summation of the total amount medium injected in a patient over time can be maintained. Signals and measurement data may be provided to an operator in the form of an audible or visual signal which can indicate to the operator of the system (i.e., a surgeon or technician) the amount of fluid injected. The signals can include a visual display of the amount injected (e.g., on a monitoring display), or a signal that may indicate to the user that a maximum amount of contrast has been injected, or that none of the medium ejected from the syringe has been received in the diversion reservoir (which may be an indication of a valve or system problem). The systems described herein also include a saline flush system. Saline volumes passing through the system should be ignored so the amount of medium injected is not incorrectly calculated. As such, the method 1800 contemplates receiving a flush signal associated with a valve of a saline flush system, operation 1810. At operation 1812, subsequent injection signals and/or diversion signals are disregarded based at least in part on the received flush signal. The injection and/or diversion signals may be ignored while the flush signal is still received, which allows the operator to flush the system without the saline volume passing through the system causing a miscalculation of the injected medium. In optional operation 1814, a position of at least one valve based at least in part on the flush signal may be adjusted, if automated valves are being utilized in the system. Otherwise, in systems where manual valves are used, the flush signal received in operation 1810 may cause a signal to be emitted, which may be used to signal an operator to close the valves not associated with the flush system (e.g., valve B and stopcock 1422 in FIG. 14). Further, it is assumed that it is understood that the order of the steps in FIG. 18 may be performed in a different order as shown without deterring from the scope of the invention. As an example, without being wholly inclusive, one might collect data from the diversion sensor before the injection sensor The monitoring systems described herein may be utilized to deliver any types of fluids to a patient during a medical procedure. Such fluids may include medium (media), agents, substances, materials, medicaments, and the like. It should be noted that these terms are used generically herein to describe a variety of fluidal materials that may include, at least in part, a substance used in the performance of a diagnostic, therapeutic or/and prophylactic medical procedure and such use is not intended to be limiting. It should be understood that the medium delivery modulation and/or measurement devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain.

The materials utilized in the manufacture of the monitoring syringe may be those typical in medical applications. Plastics such as polycarbonate may be utilized for the syringe housing and plunger. The band or gradation may be printed directly on the plunger shaft, or may be printed on a discrete plastic sheet or sheath that may then be affixed to the plunger shaft. Various types of printing may be utilized to change the translucency or opacity of the band or gradation. In some embodiments, the type of printing may be based on the type of light to be received by the sensors. For example, carbon-based printing may be utilized for sensors that detect infrared light. Thus, the band or gradation may be utilized as the filter described above.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

What is claimed is:

1. An apparatus comprising:
   a syringe housing defining an axis;
   a plunger comprising a shaft, wherein the plunger is slidably received within the syringe housing between a first position and a second position, and wherein the plunger rotatable about the axis while slidably moving from the first position to the second position during an ejection of a fluid from the syringe housing;
   at least one retainer fixed to the shaft;
   a plurality of Hall sensors;
   a circuit board secured to the at least one retainer, wherein the plurality of Hall sensors are connected to the circuit board;
   at least one battery coupled to the circuit board and configured to provide power to at least one of the plurality of Hall sensors;
   a wireless transmitter coupled to the circuit board, wherein the wireless transmitter provides wireless communication between the at least one of the plurality of Hall sensors and a signal processing device; and
   at least one magnet fixed proximate the syringe housing.

2. The apparatus of claim 1, wherein the at least one magnet comprises a plurality of magnets disposed about the syringe housing.

3. The apparatus of claim 2, further comprising a magnet retention ring disposed about the syringe housing, wherein the plurality of magnets are disposed within the magnet retention ring.

4. The apparatus of claim 1, wherein the plurality of Hall sensors are disposed linearly along the circuit board.

5. The apparatus of claim 1, further comprising:
   a switch disposed on the circuit board for selectively connecting power between the at least one battery and the at least one of the plurality of Hall sensors.

6. The apparatus of claim 5, wherein the switch is activated based on the slidable movement of the plunger.

7. The apparatus of claim 1, wherein the wireless transmitter provides wireless communication to the signal processing device so as to determine a volume of the fluid discharged from the syringe housing when the plunger is moved from the first position to the second position.

8. The apparatus of claim 1, wherein the at least one battery is replaceably secured to the circuit board.

9. The apparatus of claim 1, wherein the shaft defines a chamber, and wherein the at least one retainer is disposed within the chamber and comprises a distal retainer and a proximal retainer, wherein the circuit board is supported between the distal retainer and the proximal retainer.

10. The apparatus of claim 9, further comprising a thumb ring having a resilient base configured to be selectively engageable with the shaft at a proximate end of the shaft.

11. The apparatus of claim 10, wherein the at least one battery is disposed on the circuit board and wherein the wireless transmitter is disposed in the distal retainer.

12. The apparatus of claim 11, wherein the proximal retainer and the circuit board are removable from the chamber through the proximate end of the shaft.

13. The apparatus of claim 12, wherein the distal retainer is removable from the chamber through the proximate end of the shaft.

14. The apparatus of claim 1, wherein the plunger rotates about the axis while slidably moving from the first position to the second position.

15. An apparatus comprising:
a syringe housing defining an axis;
a plunger slidably disposed along the axis within the syringe housing, wherein the plunger defines a chamber comprising a distal end and a proximate end, and wherein the plunger rotatable about the axis during slidable movement of the plunger along the axis during an ejection of a fluid from the syringe housing;
a circuit board disposed within the chamber defined by the plunger, wherein the circuit board is configured to be inserted axially into the chamber via the proximate end;
a plurality of Hall sensors connected to the circuit board;
a wireless transmitter connected to the circuit board;
at least one battery connected to the circuit board and configured to provide power to at least one of the plurality of Hall sensors and the wireless transmitter; and
at least one magnet fixed relative to the axis, such that the slidable movement of the plunger along the axis moves at least one of the plurality of Hall sensors through a magnetic field created by the at least one magnet, wherein the at least one of the plurality of Hall sensors moving through the magnetic field produces data, wherein the data is transmitted by the wireless transmitter to a signal processor to determine a volume of the fluid displaced during the slidable movement of the plunger.

16. The apparatus of claim 15, wherein the at least one magnet comprises a plurality of magnets disposed about the axis, so as to create a substantially circular magnetic field.

17. The apparatus of claim 16, wherein the apparatus further comprises a magnet retention ring disposed about the syringe housing and wherein the plurality of magnets are disposed within the magnet retention ring.

18. The apparatus of claim 17, wherein the magnet retention ring is disposed proximate a proximal end of the syringe housing.

19. The apparatus of claim 15, further comprising:
a switch fixed to the plunger for selectively connecting power between the at least one battery and the wireless transmitter and at least one of the plurality of Hall sensors, and wherein the at least one battery is configured to provide power to the wireless transmitter.

20. The apparatus of claim 19, wherein the switch is activated based on the slidable movement of the plunger.

21. The apparatus of claim 19, wherein the switch comprises a reed switch.

22. The apparatus of claim 15, wherein the at least one of the plurality of Hall sensors is disposed so as to pass through the magnetic field at any angular position of the plunger about the axis.

23. The apparatus of claim 15, wherein the at least one magnet is secured directly to the syringe housing.

24. The apparatus of claim 15, wherein the at least one battery is replaceably secured to the circuit board.

25. The apparatus of claim 15, further comprising a distal retainer and a proximal retainer, wherein the circuit board is supported at opposite ends by the distal retainer and the proximal retainer, and wherein the proximal retainer is disposed in the chamber.

26. The apparatus of claim 15, wherein the plunger rotates about the axis during the slidable movement of the plunger along the axis.

27. An apparatus comprising:
a) a syringe housing;
b) a plunger comprising a shaft, wherein the plunger is slidably and rotatably received within the syringe housing between a first position and a second position, and wherein the shaft has certain components of a Hall Sensor module disposed within a chamber of the shaft, said certain components of the Hall Sensor module including:
i) a plurality of Hall sensors; and
ii) a circuit board, wherein the plurality of Hall sensors are connected to the circuit board;
c) at least one battery, wherein the at least one battery is configured to provide power to at least one of the plurality of Hall sensors;
d) a wireless transmitter communicatively coupled to the circuit board, wherein the wireless transmitter provides wireless communication between the at least one of the plurality of Hall sensors and a signal processing device; and
e) at least one magnet fixed proximate the syringe housing.

* * * * *